(12) United States Patent
Rasmussen et al.

(10) Patent No.: US 10,603,191 B2
(45) Date of Patent: Mar. 31, 2020

(54) ELECTROACTIVE POLYMERS AND SYSTEMS USING THE SAME

(71) Applicant: RAS Labs, Inc., Quincy, MA (US)

(72) Inventors: Lenore Rasmussen, Hingham, MA (US); Eric Sandberg, Hingham, MA (US); Simone Rodriguez, Boston, MA (US)

(73) Assignee: RAS LABS, INC., Quincy, MA (US)

( * ) Notice: Subject to any disclaimer, the term of this patent is extended or adjusted under 35 U.S.C. 154(b) by 252 days.

(21) Appl. No.: 15/521,066

(22) PCT Filed: Nov. 4, 2015

(86) PCT No.: PCT/US2015/058951
§ 371 (c)(1),
(2) Date: Apr. 21, 2017

(87) PCT Pub. No.: WO2016/073553
PCT Pub. Date: May 12, 2016

(65) Prior Publication Data
US 2017/0333223 A1    Nov. 23, 2017

Related U.S. Application Data

(60) Provisional application No. 62/074,709, filed on Nov. 4, 2014, provisional application No. 62/215,160, filed on Sep. 7, 2015.

(51) Int. Cl.
*A61F 2/78* (2006.01)
*C08F 220/06* (2006.01)
(Continued)

(52) U.S. Cl.
CPC ............. *A61F 2/7812* (2013.01); *A61F 2/80* (2013.01); *A61L 31/14* (2013.01); *C08F 220/06* (2013.01);
(Continued)

(58) Field of Classification Search
CPC .. A61F 2/7812; A61F 2/80; A61F 2002/7635; A61F 2002/5036; A61L 31/14;
(Continued)

(56) References Cited

U.S. PATENT DOCUMENTS 5,736,590 A    4/1998  Rasmussen
6,249,076 B1 *  6/2001  Madden .................. F03G 7/005
                                                    310/363
(Continued)

FOREIGN PATENT DOCUMENTS

JP    2007-510506 A    4/2007
JP    2008-515502 A    5/2008
(Continued)

OTHER PUBLICATIONS

European Search Report dated May 25, 2018, in application No. EP 15858073.8, 7 pages.
(Continued)

*Primary Examiner* — Thomas M Dougherty
(74) *Attorney, Agent, or Firm* — Wilmer Cutler Pickering Hale and Dorr LLP

(57) ABSTRACT

In one aspect, novel robust electroactive polymers (EAPs) is described, which contract and expand at low voltages to provide for a shape-morphing system, e.g., a prosthetic liner, and potentially entire prosthetic socket, to contract and expand in strategic areas as needed to maintain a comfortable and good fit throughout the day. In some embodiments, as the residual limb changes, these novel robust EAPs can change dynamically as needed to maintain a comfortable, snug fit of the prosthetic liner or socket with the hard shell of the prosthetic socket device. In some embodiments, the EAPs used in prosthetic liners or sockets can also be used to detect pressure as the device is being used, and automatically adjust to maintain fit through a control unit, so that the (Continued)

patient does not even have to stop and adjust his or her device as he or she goes about an active day.

50 Claims, 10 Drawing Sheets

(51) Int. Cl.
*H01L 41/09* (2006.01)
*H01L 41/047* (2006.01)
*F03G 7/00* (2006.01)
*A61F 2/80* (2006.01)
*A61L 31/14* (2006.01)
*C08F 290/06* (2006.01)
*A61F 2/50* (2006.01)
*A61F 2/76* (2006.01)

(52) U.S. Cl.
CPC ...... *C08F 290/062* (2013.01); *C08F 290/068* (2013.01); *F03G 7/005* (2013.01); *A61F 2002/5036* (2013.01); *A61F 2002/7635* (2013.01)

(58) Field of Classification Search
CPC .............. C08F 220/06; C08F 290/062; C08F 290/068; F03G 7/005
USPC .......................................... 310/300–371, 800
See application file for complete search history.

(56) References Cited

U.S. PATENT DOCUMENTS

| | | | |
|---|---|---|---|
| 6,768,246 B2 | 7/2004 | Pelrine et al. | |
| 6,982,514 B1 * | 1/2006 | Lu | F03G 7/005 |
| | | | 310/300 |
| 7,521,840 B2 | 4/2009 | Heim | |
| 7,595,580 B2 | 9/2009 | Heim | |
| 7,935,743 B1 | 5/2011 | Rasmussen | |
| 8,088,453 B1 | 1/2012 | Rasmussen | |
| 8,860,336 B2 | 10/2014 | Anderson et al. | |
| 9,755,135 B1 | 9/2017 | Rasmussen | |
| 2005/0102017 A1 | 5/2005 | Mattison | |
| 2007/0114116 A1 | 5/2007 | Nagai et al. | |
| 2007/0247033 A1 * | 10/2007 | Eidenschink | A61L 29/146 |
| | | | 310/311 |
| 2009/0038501 A1 | 2/2009 | Hirai | |
| 2009/0271000 A1 | 10/2009 | Altobelli et al. | |
| 2012/0032553 A1 | 2/2012 | Goyal et al. | |
| 2013/0282141 A1 | 10/2013 | Herr et al. | |
| 2016/0064643 A1 | 3/2016 | Rasmussen | |

FOREIGN PATENT DOCUMENTS

| | | |
|---|---|---|
| JP | 2009-535093 A | 10/2009 |
| WO | WO-2005/046525 A1 | 5/2005 |
| WO | WO-2006/040109 A1 | 4/2006 |
| WO | WO-2007/126520 A2 | 11/2007 |
| WO | WO-2009/038501 A1 | 3/2009 |

OTHER PUBLICATIONS

International Search Report and Written Opinion issued in the International Application: PCT/US15/58951, dated Jan. 14, 2016, 18 pages.

* cited by examiner

No Charge

Positive Electric Charge in EAP

Negative Electric Charge in EAP

No charge

Positive Charge in Central EAP

Negative Electric Charge in Central EAP

ELECTROACTIVE POLYMERS AND SYSTEMS USING THE SAME

RELATED APPLICATIONS

This application is a national stage application of International Application No. PCT/US15/58951, filed Nov. 4, 2015, which claims priority to U.S. Provisional Application 62/215,160, filed Sep. 7, 2015, and U.S. Provisional Application 62/074,709, filed Nov. 4, 2014, the contents of which are hereby incorporated by reference in their entirety.

INCORPORATION BY REFERENCE

All patents, patent applications and publications cited herein are hereby incorporated by reference in their entirety in order to more fully describe the state of the art as known to those skilled therein as of the date of the invention described herein.

TECHNICAL FIELD OF THE INVENTION

The present application generally relates to electroactive materials.

BACKGROUND

Most prosthetic liners and sockets are static. A mold of the residual limb is made, and then the prosthetic liner and socket are designed around the mold from the day of the amputee patient's fitting for the mold. The reality is that residual limbs are continually changing. In fact, most amputees' residual limbs shrink over the course of any given day (typical case), much like people's foot size changes from morning to evening.

Current prosthetic liners use a flexible material, such as a thick layer of silicone or polyurethane based material, which help to hold the liner to the residual limb by its shape (fitted to patient), some suction, and the liner's elasticity. These liners are available with or without the distal locking feature and are usually worn with traditional prosthetic socks to allow for volume adjustments. As the limb shrinks over the course of a typical day, however, there often forms a significant gap between the liner and the hard shell of the socket of the prosthetic device, which can be addressed by the patent by adding more layers of cotton socks between the liner and the hard shell. If the fit becomes too tight, the patient then removes layers of cotton socks between the liner and the hard shell. This is time-consuming and cumbersome. If the patient fails to notice that the fit is becoming too loose or too tight, tissue damage can occur to the residual limb. Because the skin of the leg (below the knee amputee) and thigh (above the knee amputee) do not have many nerves compared to hands and feet, the patient often does not notice a poor fit until there is a problem, and in the case of slippage, even bleeding from abrasion, due to these areas of the body being relatively uninervated.

To address the maintenance of prosthetic liner and socket fit beyond a flexible liner, several strategies have been explored, such as a variety of suction and vacuum systems. Suction systems often consist of a soft liner equipped with a one-way valve and a sealing sleeve. The patient inserts his or her liner-covered limb into the socket and the application of body weight as he or she stands expels excess air through the valve. In a typical vacuum system, a sleeve creates a seal around the top edge of the socket, then a pump and exhaust valve remove virtually all air between the socket and the liner as the patient wears the device. This system regulates the vacuum level within a defined range. Benevolent Technologies uses a pump to pull vacuum around gelled beads to produce a form-fitting one-size-fits-all fit. Challenges from vacuum systems is that patients often don't like the feel and simply don't feel as secure using their prosthetic devices as compared to more traditional prosthetic liner systems. Vacuum systems provide a stronger fit than suction systems, but with vacuum systems, if the vacuum is too tight and restrictive, tissue damage can occur in the residual limb.

The modeling of a perfect fit prosthetic socket is complex and unique for each patient. The modeling for sockets, and test case uses, is currently being performed in Prof. Hugh Herr's Biomechatronics Laboratory at MIT, by Prof. Herr, the founder of iWalk, now Biom, with a custom fit socket (U.S. Ser. No. 13/836,835); however, this is a relatively static system with respect to fit. Humans are dynamic, particularly when in motion, and undergo marked changes from an initial prosthetic fitting, even with state-of-the-art modeling and design.

Smart materials have found used as sensors, such as using dielectric elastomeric actuators (DEAs) as sensors and self-sensors. Dielectric materials are poor conductors of electricity, but good at supporting electrostatic fields, so act as capacitors. SRI international, Artificial Muscle Inc., and Stretch Sense/University of Auckland have found that DEAs have the potential for sensing and for self-sensing, where self-sensing is sensing an electrical property of the actuator itself (U.S. Pat. Nos. 8,860,336, 7,521,840, 7,595,580, 6,768,246). The state of a DEA can be determined by sensing the capacitance between the electrodes. Due to the high voltages (kV range) applied to the electrodes which are necessary to actuate a DEA, implementing capacitive self-sensing is not as simple as applying the capacitive sensing techniques commonly applied in other fields. The methodology for self-sensing in DEAs is very complex.

SUMMARY

Described herein is electroactive polymers or electroactive ionic polymers (used interchangeably herein and both can be referred to as EAPs) that contract and expand to provide for a shape-morphing system. In some embodiments, a prosthetic device such as a prosthetic liner or socket including the shape-morphing system is described. In some embodiments, the EAPs in the prosthetic liner contracts and expands in strategic areas as needed to maintain a comfortable and good fit throughout the day. This technology can be used to enhance flexible liners to be more shape adaptive, or could be tailored or even 3D-printed to produce comfortable and adaptive custom fit prosthetic liners and sockets. The prosthetic device described herein is superior to traditional, suction, and vacuum prosthetic liner and socket systems because of feel, comfort, and adaptive maintenance of the just-right safe fit. The instant invention allows for implementation with current prosthetic liners, or could be used for the entire prosthetic socket liner, where different areas may have different softness/hardness, and different shape-morphing abilities, to provide custom comfort and fit.

In one aspect, a prosthetic device comprising one or more shape-morphing systems disclosed herein is described, which is designed to keep amputees, particularly children, active and in motion so that they are fully engaged in life, to allow amputees to no longer be disabled. The prosthetic device described herein may allow people who have lost limbs or who were born without fully developed limbs to easily go about their day, including an energetic, active life style, without having to adjust or even think about their prosthesis. The prosthetic device as described herein enables human to move, work, and play as one, naturally, the way we are designed to be. As the residual limb changes (common occurrence even over the course of a day), the robust EAPs described herein can change dynamically as needed to maintain a comfortable, snug fit of the prosthetic liner or socket with a hard body, e.g., the hard shell of the prosthetic socket. In addition, the robust EAPs described herein can easily serve dual use as pressure sensors. By tracking the impedance of these EAPs, and thus the mechanical pressure exerted on these EAPs in the prosthetic liner or socket, if the fit becomes too tight or too loose, the EAPs, using feedback loop circuitry, could automatically adjust to maintain a good fit, without the patient having to stop to adjust the fit or to even have to think about their prosthetic device as they go about their active life. This EAPs and devices described herein can also be applied to other void-filling and shape-morphing applications. The embodiments described herein will advance the state of care for amputees and for people born without fully developed limbs. For children, this is of paramount importance for the brain mapping that occurs with full function during childhood, and for all children to comfortably and easily enjoy the full freedom of motion as they grow.

In one aspect, an electroactive polymer shape-morphing system is described, including:

a first electrode;

a second electrode counter to the first electrode and spaced apart from the first electrode;

an ionically conductive fluid; and a first actuator electrically connected to the first electrode and comprising a first electroactive ionic polymer, said electroactive polymer selected to expand or contract on application of an electrical potential, and said first actuator spaced apart from and in fluidic communication with the second electrode In any one of the embodiments described herein, the shape-morphing system further includes an electrically conducting backing disposed along and in electrical contact with a surface of the first actuator, wherein one or both of the first actuator or the backing is electrically connected to the first electrode.

In any one of the embodiments described herein, the surface of the first actuator is bonded to the conducting backing to restrict the contraction or expansion of the first actuator in a direction parallel to the surface.

In any one of the embodiments described herein, the first actuator is configured to contract or expand in a direction perpendicular to the surface.

In any one of the embodiments described herein, the first electroactive ionic polymer is selected to expand or contract in a predetermined direction.

In any one of the embodiments described herein, the actuator has an area and a transverse thickness and the first electroactive ionic polymer is selected to expand or contract the thickness of the actuator.

In any one of the embodiments described herein, the shape-morphing system further includes a fluid reservoir in fluidic communication with the first electroactive ionic polymer and connected to the second electrode.

In any one of the embodiments described herein, the fluid reservoir comprises a fluid absorption pad or an open cell foam for containing the fluid.

In any one of the embodiments described herein, the ionically conductive fluid is an aqueous solution of a salt.

In any one of the embodiments described herein, the shape-morphing system further includes a second actuator comprising a second electroactive ionic polymer, said second actuator electrically connected to the second electrode and spaced apart from and in fluidic communication with the first electroactive ionic polymer, wherein the first and second electroactive ionic polymers are the same or different.

In any one of the embodiments described herein, the first electroactive ionic polymer is selected to expand and the second electroactive ionic polymer is selected to contract along predetermined directions on application of an electrical potential to the first and second electrodes.

In any one of the embodiments described herein, the first electroactive ionic polymer is selected to contract and the second electroactive ionic polymer is selected to expand along predetermined directions on application of an electrical potential to the first and second electrodes.

In any one of the embodiments described herein, the first actuator is in a shape selected from the group consisting of sheet, pad, sphere, cylinder, cone, pyramid, prism, spheroid ellipse, ellipsoid, rectangular prism, toroid, parallelepiped, rhombic prism and a combination thereof.

In any one of the embodiments described herein, the first actuator comprises one or more electroactive ionic polymer sheets.

In any one of the embodiments described herein, each electroactive ionic polymer sheet is in electrical contact with a conductive layer electrically connected to the first electrode.

In any one of the embodiments described herein, the conductive layer is made from a material selected from the group consisting of metal, carbon, and a combination thereof.

In any one of the embodiments described herein, the first electroactive ionic polymer is selected from the group consisting of polymethacrylic acid, poly2-hydroxyethyl methacrylate, poly(vinyl alcohol), ionized poly(acrylamide), poly(acrylic acid), poly(acrylic acid)-co-(poly(acrylamide), poly(2-acrylamide-2-methyl-1-propane sulfonic acid), poly(methacrylic acid), poly(styrene sulfonic acid), quarternized poly(4-vinyl pyridinium chloride), poly(vinylbenzyltrimethyl ammonium chloride), sulfonated poly(styrene-b-ethylene-co-butylene-b-styrene), sulfonated poly(styrene), and a combination thereof.

In any one of the embodiments described herein, the second electroactive ionic polymer is selected from the group consisting of polymethacrylic acid, poly2-hydroxyethyl methacrylate, poly(vinyl alcohol), ionized poly(acrylamide), poly(acrylic acid), poly(acrylic acid)-co-(poly(acrylamide), poly(2-acrylamide-2-methyl-1-propane sulfonic acid), poly(methacrylic acid), poly(styrene sulfonic acid), quarternized poly(4-vinyl pyridinium chloride), poly(vinylbenzyltrimethyl ammonium chloride), sulfonated poly(styrene-b-ethylene-co-butylene-b-styrene), sulfonated poly(styrene), and a combination thereof.

In any one of the embodiments described herein, the first electroactive ionic polymer is cross-linked with one or more cross-linking polymer agents each selected from the group consisting of a poly(dimethylsiloxane) (PDMS) dimethacrylate chain, a poly(ethylene glycol) dimethacrylate chain, an ethylene glycol dimethacrylate, 1,1,1-trimethylolpropane trimethacrylate, and a combination thereof.

In any one of the embodiments described herein, the first electroactive ionic polymer is cross-linked with one or more elastomeric cross-linking polymer agents.

In any one of the embodiments described herein, the first electroactive ionic polymer is cross-linked with a first cross-linking polymeric chain comprising a poly(dimethylsiloxane) (PDMS) dimethacrylate chain.

In any one of the embodiments described herein, the first electroactive ionic polymer is cross-linked with a first cross-linking polymeric chain comprising a poly(dimethylsiloxane) (PDMS) dimethacrylate chain and a second crossing linking polymeric agent different from the first cross-linking polymeric agent.

In any one of the embodiments described herein, the second cross-linking polymeric agent is selected from the group consisting of a poly(ethylene glycol) dimethacrylate chain, an ethylene glycol dimethacrylate chain, 1,1,1-trimethylolpropane trimethacrylate, and a combination thereof.

In any one of the embodiments described herein, the first and/or second electrodes are flexible, bendable or stretchable electrodes.

In any one of the embodiments described herein, the first and/or second electrodes are spiral-shaped or spring-shaped.

In any one of the embodiments described herein, the first and/or second electrodes are made from a material selected from the group consisting of metal, carbon, other conductive materials, and a combination thereof.

In any one of the embodiments described herein, the shape-morphing system further includes an electroconductivity-enhancing material in ionic communication with the first electroactive ionic polymer.

In any one of the embodiments described herein, the electroconductivity-enhancing material is selected from the group consisting of solvent, electrolyte solution, electrolyte gel formulation, carbon particles, conductive fibers, preceding weaves, preceding felts, preceding nano-particles, preceding nanotubes, metal ions, salt, and a combination thereof.

In any one of the embodiments described herein, the shape-morphing system further includes a power source.

In any one of the embodiments described herein, the power source is a rechargeable or non-rechargeable battery pack.

In any one of the embodiments described herein, the shape-morphing system is in a form selected from the group consisting of fibers, bulk, slabs, bundles, and combinations thereof.

In any one of the embodiments described herein, the shape-morphing system is configured for filling a void between the first actuator and a target element.

In any one of the embodiments described herein, the shape-morphing system is configured for securing or engaging a target element.

In another aspect, a liner for securing a limb in a prosthetic device or a prosthetic socket is described, including:
 a flexible layer configured to surround a limb of a patient or conform to the inside circumference of a prosthesis; and
 at least one shape-morphing system of any one of the embodiments described herein embedded in the flexible layer and configured to secure or engage a limb of a patient.

In any one of the embodiments described herein, the flexible layer is made of silicone.

In any one of the embodiments described herein, the liner or prosthetic socket comprises a plurality of the shape-morphing systems each of any one of the preceding claims and embedded in the flexible layer; wherein the shape-morphing systems are fluidically isolated from each other and arranged around the limb of a patient to secure the limb.

In any one of the embodiments described herein, the prosthesis has a hard body and upon the application of an electrical potential to the first electrode, the first actuator is configured to expand against the hard body towards the limb of the patient.

In any one of the embodiments described herein, the liner or prosthetic socket further includes a control unit configured to receive or measure the impedance and/or the pressure of the first electroactive ionic polymer.

In any one of the embodiments described herein, the control unit automatically adjusts the voltage of the first electrode to adjust the pressure of the first electroactive ionic polymer.

In any one of the embodiments described herein, the control unit is configured to adjust the pressure to a pre-determined value or a pre-set value.

In yet another aspect, an actuation device is described, including one or more of the shape-morphing systems of any one of the embodiments described herein, wherein upon the application of an electrical potential to the first electrode, the first electroactive ionic polymer is configured to expand or contract to generate an actuation force to result in a movement of the first actuator to move from a first position to a second position.

In yet another aspect, a method of operating a prosthesis is described, comprising:
 providing a prosthesis having a hard body;
 providing the liner of any one of the embodiments described herein,
 providing an electrical potential to the first electrode to
  contract the first electroactive ionic polymer to adjust the fit of the prosthesis to a patient's limb; or
  expand the first electroactive ionic polymer material against the hard body towards the limb of the patient and secure the limb.

In any one of the embodiments described herein, the voltage is less than about 1.23 V.

In any one of the embodiments described herein, the method further includes measuring or receiving the pressure of the first electroactive ionic polymer through a control unit.

In any one of the embodiments described herein, the method further includes automatically adjusting the voltage to maintain the pressure to a pre-determined or pre-set value.

It is contemplated that any embodiment disclosed herein may be properly combined with any other embodiment disclosed herein. The combination of any two or more embodiments disclosed herein is expressly contemplated.

As used herein, the use of the phrase "polymer" includes, but is not limited to, the homopolymer, copolymer, terpolymer, random copolymer, and block copolymer. Block copolymers include, but are not limited to, block, graft, dendrimer, and star polymers. As used herein, copolymer refers to a polymer derived from two monomeric species; similarly, a terpolymer refers to a polymer derived from three monomeric species. The polymer also includes various morphologies, including, but not limited to, linear polymer, branched polymer, random polymer, crosslinked polymer, and dendrimer systems. As an example, polyacrylamide polymer refers to any polymer including polyacrylamide, e.g., a homopolymer, copolymer, terpolymer, random copolymer, block copolymer or terpolymer of polyacrylamide. Polyacrylamide can be a linear polymer, branched polymer, random polymer, crosslinked polymer, or a dendrimer of polyacrylamide.

As used herein, the phrase "ionic polymer" refers to any polymer which has one or more ionizable groups. Non-limiting examples of the ionic polymers include a polymer of one or more ionic-group containing monomers. Other non-limiting examples of the ionic polymers include a polymer which one or more ionic groups at any positions of the polymeric chain. As used herein, the phrase "electroactive ionic polymer" refers to any polymer which has one or more ionizable groups and can shape-change, e.g., expand or contract, upon the application of a voltage.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments. Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "linked to," "on," "connected to," "coupled to," "in contact with," etc., another element, it may be directly linked to, on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

DESCRIPTION OF THE DRAWINGS

The invention is described with reference to the following figures, which are presented for the purpose of illustration only and are not intended to be limiting. In the Drawings.

DETAILED DESCRIPTION

Figure 1A:
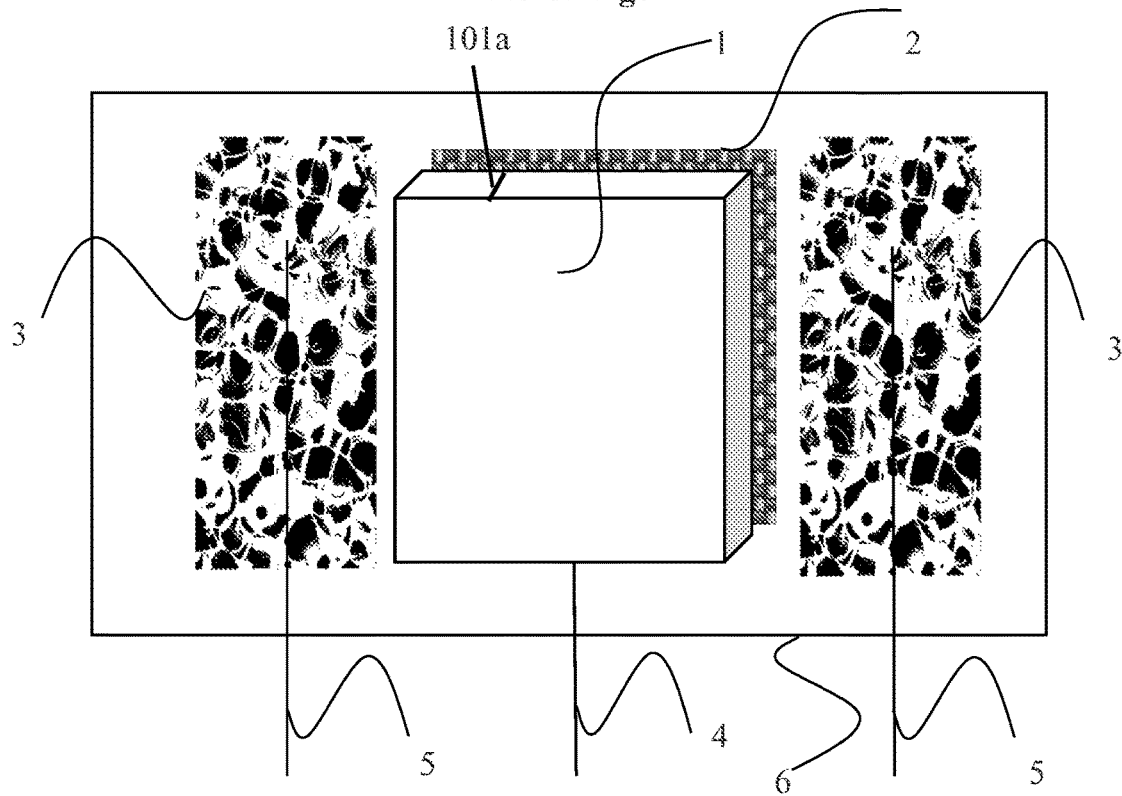
FIG. 1A is a perspective view of an encapsulated electroactive polymer (EAP) shape-morphing sheet system, with one EAP sheet subjected to no voltage, and with two fluidic reservoirs comprising preferably of open cell foam, according to one or more embodiments described herein.

In one aspect, an electroactive polymer shape-morphing system is described, including:
a first electrode;
a second electrode counter to the first electrode and spaced apart from the first electrode;
an ionically conductive fluid; and
a first actuator electrically connected to the first electrode and comprising a first electroactive ionic polymer, said electroactive polymer selected to expand or contract on application of an electrical potential, and said first actuator spaced apart from and in fluidic communication with the second electrode.

In certain embodiments, the shape-morphing system further includes an electrically conducting backing or a conductive layer disposed along and in electrical contact with a surface of the first actuator, wherein one or both of the first actuator or the backing is electrically connected to the first electrode. The conducting backing or a conductive layer may be bonded to a surface of the first actuator. Any level of bonding is contemplated. In certain embodiments, the first actuator and/or the first electroactive ionic polymer are selected to expand or contract in a predetermined direction. In certain specific embodiments, the EAP sheet/pad is bonded to the conductive backing which restrict the expansion or contraction in 2 directions (e.g., in the directions parallel to the surface plane of the backing), which allows for a more movement in the unrestricted direction, for example, allowing for greater changes in thickness (i.e., in the directions perpendicular to the surface plane of the backing, which is the desired direction of change in the central EAP pads. In certain specific embodiments, the first actuator has an area and a transverse thickness and the first electroactive ionic polymer is selected to expand or contract the thickness of the actuator.

In another aspect, a liner for securing a limb in a prosthetic device or a prosthetic socket is described, including: a flexible layer configured to surround a limb of a patient or conform to the inside circumference of a prosthesis; and at least one shape-morphing system according to any one of the embodiments described herein embedded in the flexible layer and configured to secure or engage a limb of a patient. In certain embodiments, the liner or the prosthetic device includes a flexible layer; and at least one shape-morphing system disclosed herein embedded in the flexible layer and configured to secure or engage a limb of a patient. The flexible layer may be made of silicone. In other embodiments, the prosthetic device comprises a plurality of the shape-morphing systems disclosed herein; wherein the shape-morphing systems are fluidically isolated from each other and strategically arranged around the limb of a patient to secure the limb. For instance, the shape-morphing system can each be an isolated pouch embedded in the flexible layer. The arrangement of the plurality of the shape-morphing systems can be determined by the size and type of the limb to ensure that the limb is securely and comfortably fit to the prosthetic device. In certain specific embodiments, the prosthesis may have a hard body and upon the application of an electrical potential to the first electrode and the first actuator is configured to expand against the hard body towards the limb of the patient. In certain embodiments, the prosthetic liner described herein can be used together with traditional hard prosthetic device, e.g., a hard body such as a prosthetic hand, arm, foot or leg. In certain embedment, upon the application of an electrical potential to the first electrode, the first electroactive ionic polymer is configured to expand against the hard body towards the limb of the patient to secure the limb.

In some embodiments, the first and second electroactive ionic polymers, as described herein, are ionizable polymers which can contract or expand when subjected to an electrical potential or voltage. Suitable compositions of the first and second electroactive ionic polymers are described in further detail below. In certain embodiments, the electroactive ionic polymers contract when subjected to a positive voltage and expand when subjected to a negative voltage. In certain embodiments, the actuator has an area and a transverse thickness and the first electroactive ionic polymer is selected to expand or contract the thickness of the actuator.

In certain embodiments, the shape-morphing system may further include a fluid reservoir in fluidic and/or ionic communication with the first electroactive ionic polymer and connected to the second electrode. The fluid reservoir area may be in fluidic and/or ionic communication with the first electroactive ionic polymer and connected to the second electrode counter to the first electrode. The ionically conductive fluid may be an aqueous solution of a salt.

Both the first and second electrodes may be connected to a power source to complete the electrical circuit. In certain embodiments, the shape-morphing system further comprises a fluid absorption pad or an open cell foam. However, any other system or device configured to retain or store fluid can be used. The fluid may be water or an aqueous solution of an inorganic or organic salt. Upon contact and/or absorption of the fluid from the fluid reservoir area, the first electroactive ionic polymer becomes electrically conductive and will undergo expansion or contraction depending on the voltage of the first electrode. In certain embodiments, for a small, gradual movement of the EAP pads, low voltage is used, preferably less than 1.23 V in order to eliminate any electrophoretic effects. In certain embodiments, for contraction of the central EAP(s), its embedded electrode should carry a positive voltage charge, and the external to the central EAP(s) should have a negative voltage charge. In other embodiments, conversely, for expansion of the central EAP(s), its embedded electrode should carry a negative voltage charge, and the external to the central EAP(s) should have a positive voltage charge.

In other embodiments, the shape-morphing system further includes a second actuator comprising a second electroactive ionic polymers electrically connected to the second electrode and spaced apart from and in fluidic communication with the first electroactive ionic polymer, wherein the first and second electroactive ionic polymers are the same or different. When the first and second electroactive ionic polymers are the same polymers, they may be connected to two electrodes with opposite voltages and thus have two opposite motions: the first electroactive ionic polymer is selected to expand along a predetermined direction when connected to the first (e.g., negative) electrode, and the second (e.g., positive) electroactive ionic polymer is selected to contract along a predetermined direction when connected to the second electrode or vice versa. In certain embodiments, the prosthetic liner including the shape-morphing system has an expansion area (e.g., an area having the first electroactive ionic polymer is subjected to a negative voltage) and a contraction area (e.g., an area having the second electroactive ionic polymer subjected to a positive voltage). Such prosthetic liners can be designed to have different movements at the different portions of the limb as needed. In other embodiments, the first and second electroactive ionic polymers are not the same polymers and their reaction to the positive/negative voltages can be the same or different. In certain embodiments, the fluid as described herein provides the fluidic and ionic communication between the first and second electroactive ionic polymers. Thus, when the first and second electroactive ionic polymers are connected to the first and second electrodes connected to a power source, the electrical circuit is complete.

In some embodiments, the first actuator and/or second actuator are in a shape selected from the group consisting of sheet, pad, sphere, cylinder, cone, pyramid, prism, spheroid ellipse, ellipsoid, rectangular prism, toroid, parallelepiped, rhombic prism and a combination thereof. Another form factors known in the art are contemplated. In some embodiments, the first and/or second electroactive ionic polymers are in the form of one or more sheets or pad. In certain embodiments, the first and/or second electroactive ionic polymers are in electrical contact with a conductive layer and connected to the first and/or second electrodes through the conductive layer. In some specific embodiments, the first and/or second actuators or electroactive ionic polymers are in the form of a plurality of sheets or pad separated by one or more conductive layers each connected to the respective first or second electrode. Without wishing to be bound by any particular theory, it is believed that the inclusion of a plurality of the electroactive ionic polymer pad or sheet each connected to the same electrode via conductive layer shortens the length that ion has to travel and thus improves the overall ion-conductivity and efficiency and conductivity of the shape-morphing system.

In certain embodiments, the conductive layer is plasma treated or etched. In certain specific embodiments, the conductive layer is made from a material selected from the group consisting of metal, carbon, and a combination thereof. The first and/or second electrodes may be flexible, bendable or stretchable electrodes, which can be spiral-shaped or spring-shaped. The first and/or second electrodes can be made from a material selected from the group consisting of metal, carbon, other conductive materials, and a combination thereof. Other materials known in the art and suitable for use as electrodes are contemplated.

In certain embodiments, the first and/or second electrodes are configured to be connected to a power source. The power source can be part of the shape-morphing system or the prosthetic liner or socket. For instance, the power source can be a battery or battery pack, which can be rechargeable or non-rechargeable, as part of the shape-morphing system or the prosthetic liner or socket.

In certain specific embodiments, the prosthetic liner comprises two or more EAP pad/sheet shape-morphing systems. In other embodiments, the prosthetic liner comprises a single EAP pad/sheet shape-morphing system. The EAP pad/sheet shape-morphing system may be placed in strategic positions around a limb, preferably with two, three, or four EAP pad/sheet systems placed around a limb. Alternatively, the prosthetic liner may include a single continuous EAP pad/sheet surrounding the whole limb, where any area can be controlled and adjusted by the patient to produce a just right feeling fit. In certain embodiments, the shape-morphing system is in a form selected from the group consisting of fibers, bulk, slabs, bundles, and combinations thereof.

In certain embodiments, the shape-morphing system further comprises an electroconductivity-enhancing material in ionic communication with the first electroactive ionic polymer or as part of the composition of the first electroactive ionic polymer. For instance, the EAPs can be treated post-synthetically with additives to improve the electroactivity. Non-limiting examples of the additives include salt and solvent. In certain embodiments, alternatively or in addition to solvent, electrolyte solution or electrolyte gel formulation, carbon particles, fibers, weaves, felts, nano-particles, nano-tubes, metal ions, salts, organic salts, any other electrically conductive material, or combinations thereof, may be present in the EAP or encapsulated EAP shape-morphing pad systems to enhance electroactivity or conductivity.

In some embodiments, the electroactive polymer further includes one or more salts. In certain embodiments, the salt is acetate salts. In certain embodiments, the acetate salt is selected from the group consisting of methacrylic acetate sodium salt, methacrylic acetate potassium salt, isobutyrate sodium salt, isobutyrate potassium salt, 2-methyl propoanate sodium salt, 2-methyl propoanate potassium salt, other similar organic acetate salts, and combinations thereof. Without wishing to be bound by any particular theory, it is believed that the addition of one or more salts further increase the electric conductivity of the EAP and thus further improves the efficiency of the actuating system.

For current prosthetic liners and sockets to automatically determine fit, pressure gauges or systems may be needed. In certain embodiments, the shape-morphing system or the prosthetic liner or socket described herein further includes one or more control units. In some embodiments, the control unit is configured to control the voltage of the first and/or second electrodes. The control unit may also be configured to measure or receive the impedance of the EAP and/or the pressure information (e.g., to receive the pressure information from the sensor or derive the information from the measured impedance of the EAP material). In some specific embodiments, part of the role of the battery pack can be for feedback. Feedback can be provided by either small pressure gauges in the adjustable liner or socket, or can be provided by impedance feedback from the EAPs themselves. In some embodiments, the EAPs in the instant invention can serve dual use as pressure sensors. In some embodiments, because these EAPs, in order to be electroactive, need to be moist and contain an electrolyte, these EAPs are neither pure electrical insulators nor pure electrical conductors, and have some inherent resistance. When mechanical pressure is applied to these EAPs, the impedance changes can be easily detected. In some embodiments, because these EAPs have different electrical impedance values when compressed (mechanical stress) or uncompressed (relaxed with no mechanical stress), this can be used to provide data back to a controller or control unit, to mediate and control the amount of expansion or contraction as needed, using low voltage electric input from the battery pack. In some embodiments, these EAPs, used in prosthetic liners or sockets to maintain perfect fit, can also be used in a controlled loop to detect pressure as the device is being used, and automatically adjust to maintain fit, because pressure can be detected by the EAP and then the EAP adjusted automatically from its own feedback. When the prosthetic device includes a plurality of the shape-morphing systems, the prosthetic device may include one control unit controlling all of the shape-morphing systems. Alternatively, the prosthetic device may include more than one control units each independent controlling one or more of the shape-morphing systems.

Thus, in certain embodiments, pressure sensing occurs from impedance changes in the EAP itself under mechanical pressure. Without being wishing to be bound by any particular theory, it is believed that as the EAP is compressed, the impedance decreases. Thus, in certain embodiments, the EAP described herein can be used also as pressure sensors, e.g., dual use as resistive pressure sensors, which could be used to provide controlled loop feedback for automatic comfort and good fit throughout the day.

Alternatively, the EAP pad/sheet can further includes a pressure sensor to detect the pressure inside the EAP pad/sheet or at the surface of the EAP pad/sheet when the EAP pad/sheet is in contact with a patient's limb or other body parts.

In some embodiments, the control unit is configured to adjust the voltage to the first and/or second electrodes to adjust the size of the EAP pad/sheet based on a user's input. The control unit may be configured to adjust the pressure to a pre-determined value or a pre-set value. In other embodiments, the control unit is configured to automatically adjust the voltage of the first and/or second electrodes to expand or contract the EAP pad/sheet to maintain a pressure value (e.g., a pre-determined comfortable pressure value set by the patient, the user, or the manufacturer). This way a patient wearing the prosthetic liner disclosed herein doesn't even have to think about their prosthetic device as it automatically adjusts during his or her active life. In certain embodiments, the prosthetic liner or socket also includes manual control so the patient can override the automatic adjustment if needed. Unlike static systems, the instant invention allows for fit and comfort that is adaptable as the residual limb changes, by using electroactive polymeric shape-morphing pads within the prosthetic liner, or as the entire socket, which can maintain comfort and fit with ease, either from manual control, or by tying into the pressure sensing of these EAPs, which could automatically adjust to maintain comfort and fit.

In some embodiments, the control unit may control the specific voltage of the first and/or second electrodes. In certain embodiments, the control unit may also control the voltage of the first and/or second electrodes to be positive or negative electrode.

In some embodiments, the shape-morphing system is configured for filling a void between the first actuator and a target element. In other embodiments, the shape-morphing system is configured for securing or engaging a target element.

In some embodiments, the shape-morphing system disclosed herein can be adjusted manually with a device or a control unit on the prosthesis, socket, or liner, adjusted remotely such as through Bluetooth or Wi-Fi by a phone app or other application, by pressure sensing feedback, or any combination thereof.

The various features disclosed herein are explained in further detail with references to the Figures below, which are the non-limiting embodiments of this disclosure.

FIG. 1A shows an encapsulated electroactive polymer (EAP) shape-morphing sheet system at rest (i.e., with no applied potential), where 1 is the EAP based shape-morphing sheet having its resting thickness 101*a*. 2 is a conductive backing to EAP sheet, which with any level of bonding to the EAP sheet. The use of the conductive backing or layer may reduce the length of the path that electrons and ions have to travel and thus increase the circuit efficiency. Upon the application of a potential, the electroactive polymer expands and provides for a preferential change in thickness of the EAP pad (see FIG. 1B). 3 is reservoir areas for fluid, typically water, that absorb or provide moisture from or to the EAP sheet 1 as it shape-morphs.

Figure 1B:
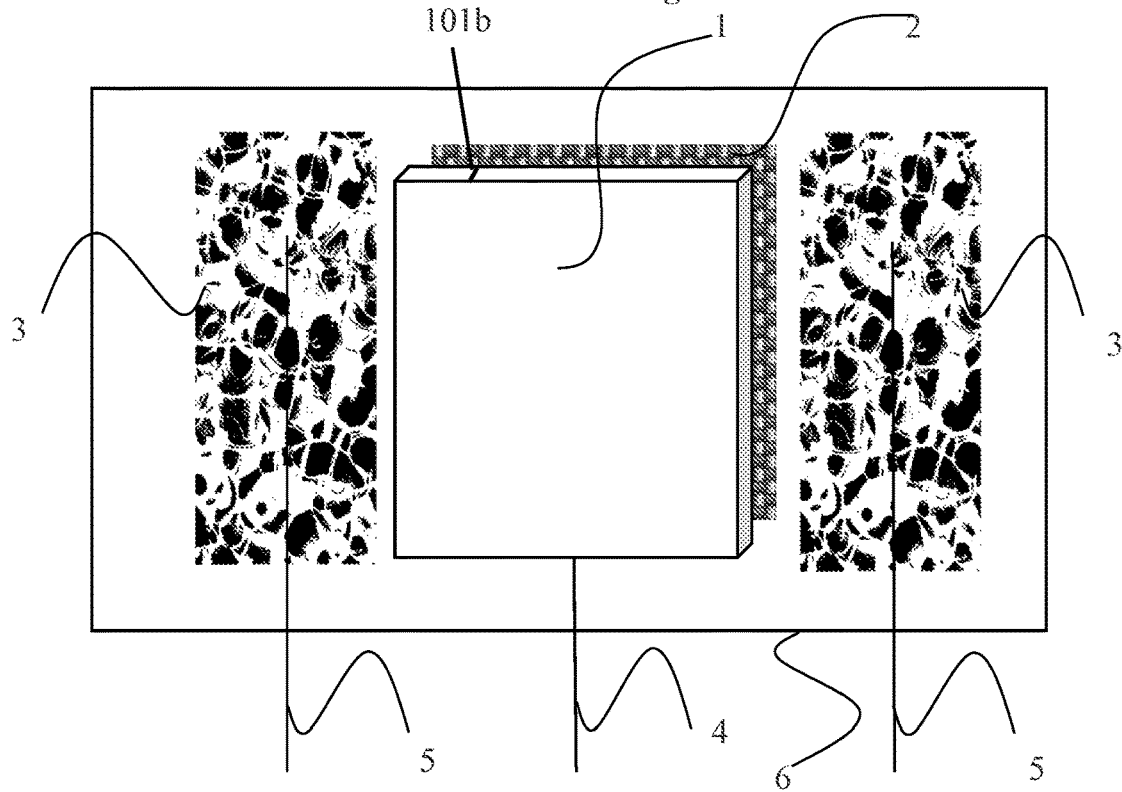
FIG. 1B is a perspective view of an encapsulated electroactive polymer (EAP) shape-morphing sheet system, with one EAP sheet subjected to a positive voltage, and with two fluidic reservoirs comprising preferably of open cell foam, according to one or more embodiments described herein.
Figure 1C:
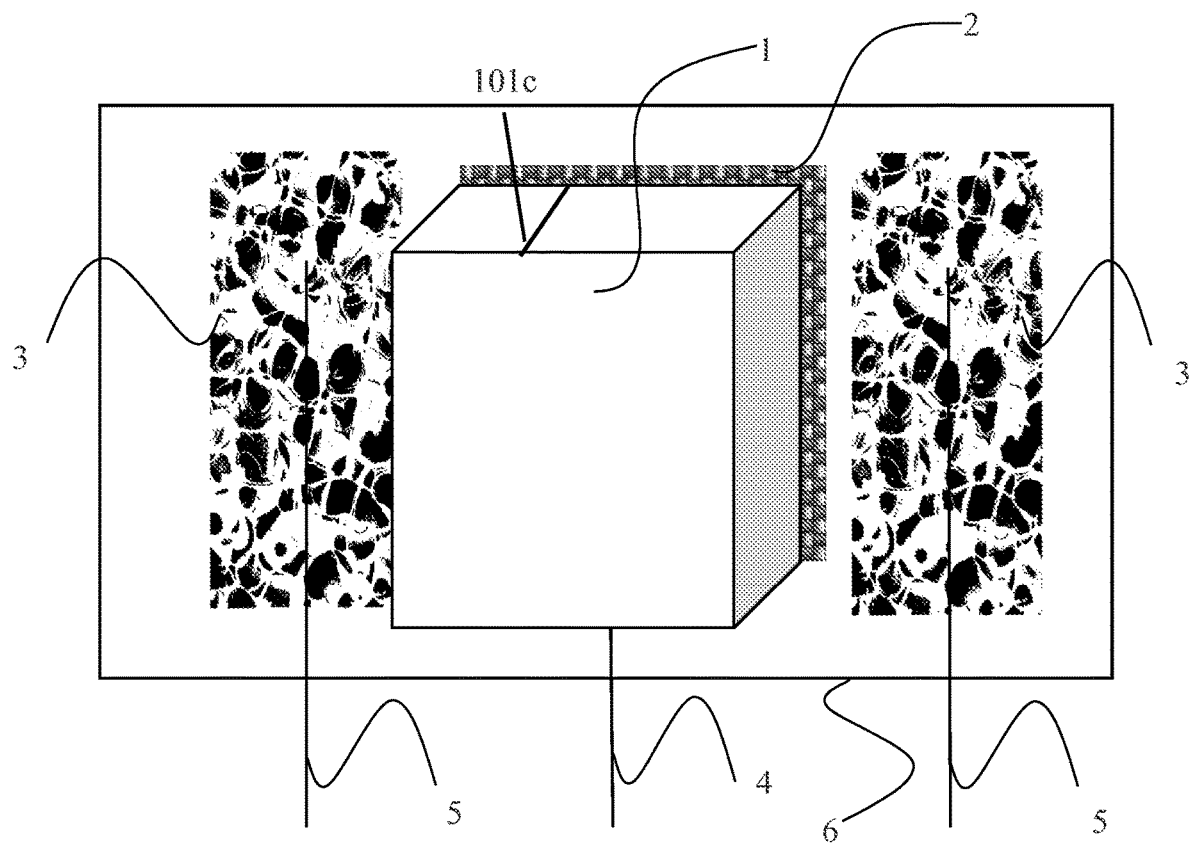
FIG. 1C is a perspective view of an encapsulated electroactive polymer (EAP) shape-morphing sheet system, with one EAP sheet subjected to a negative voltage, and with two fluidic reservoirs comprising preferably of open cell foam, according to one or more embodiments described herein.

During operation, as shown in FIG. 1B, the EAP sheet may contract under positive voltage so that its thickness 101*b* is smaller than its resting thickness 101*a*; alternatively, in FIG. 1C, the EAP sheet expands under negative voltage so that its thickness 101*c* is larger than its resting thickness 101*a*. The reservoir areas are preferably open cell foams. 4 is the electrode connecting to the conductive backing to the EAP sheet and to an electric power source (not shown). 5 is the counter electrode, conducting the opposite electric polarity charge of electrode 4, connected to the fluidic reservoir areas 3 and to an electric power source (not shown), and 6 is a flexible layer (e.g., a flexible coating layer) of the EAP shape-morphing sheet system comprising preferable medical grade silicone, encapsulating the EAP shape-morphing system. The flexible or bendable electrodes may extend out of the EAP shape-morphing sheet system, but the flexible or bendable electrodes may be continued within the flexible prosthetic liner to be connected to a power source embedded in the shape-morphing sheet system or in the prosthetic device. The power source may be a rechargeable or non-rechargeable battery pack.

Figure 2A:
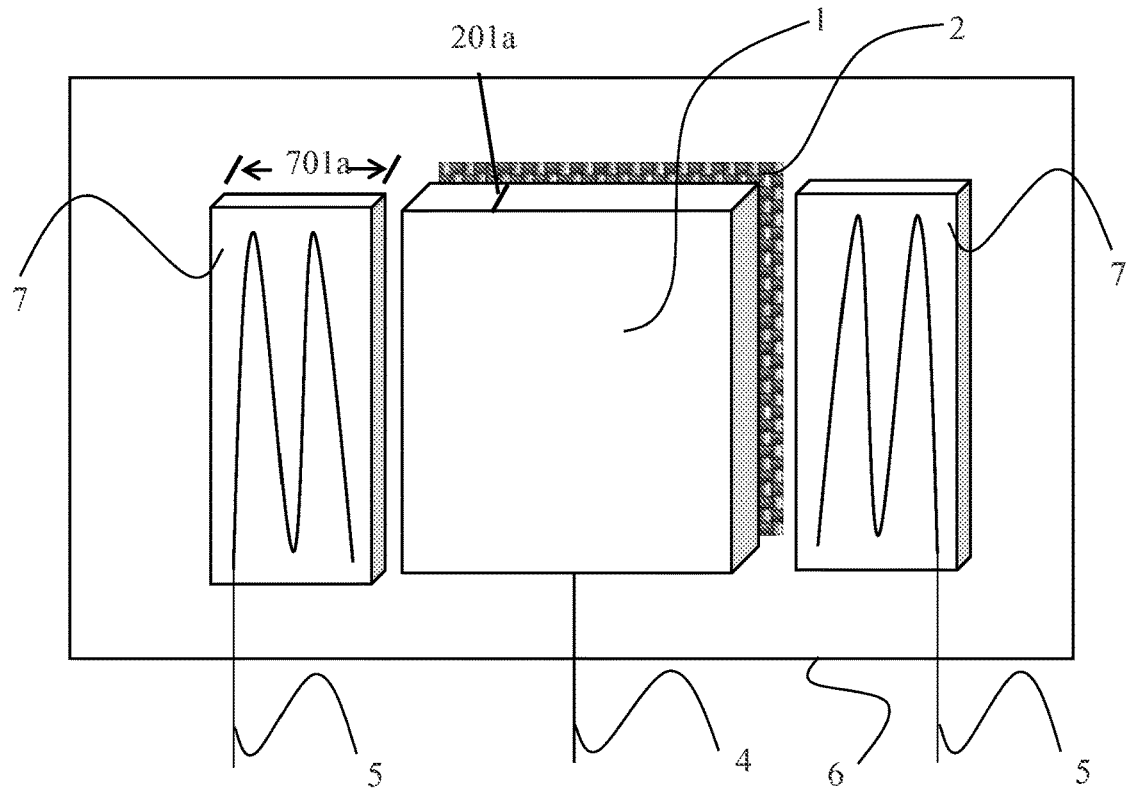
FIG. 2A is a perspective view of an encapsulated EAP shape-morphing sheet system, with one EAP sheet subjected to no voltage and two EAP areas wired for complimentary opposable motion, according to one or more embodiments described herein.

FIG. 2A shows an encapsulated EAP shape-morphing sheet system at rest (i.e., with no applied potential), where 1 is the EAP based shape-morphing sheet having a resting thickness of 201*a*. 2 is the conductive backing to EAP sheet, which with any level of bonding to the EAP sheet, provides for a preferential change in thickness of the EAP sheet under voltage. 7 is another EAP sheet having a resting width of 701*a*, which absorbs or provides moisture from or to the EAP sheet 1 as it shape-morphs. These areas are preferably EAPs with flexible or bendable wiring that allows for change in the thickness of these EAP areas. 4 is the electrode connecting to the conductive backing to the EAP sheet and to an electric power source (not shown). 5 is the counter electrode connected to the EAP area 7 and to an electric power source (not shown). 6 is a flexible layer (e.g., a flexible coating layer) of the EAP shape-morphing pad system comprising preferable medical grade silicone, surrounding above and below and all sides of the EAP shape-morphing system, with flexible or bendable electrodes extending out of the EAP shape-morphing system, but where the flexible or bendable electrodes may be continued within the flexible prosthetic liner to be connected to a power source.

Figure 2B:
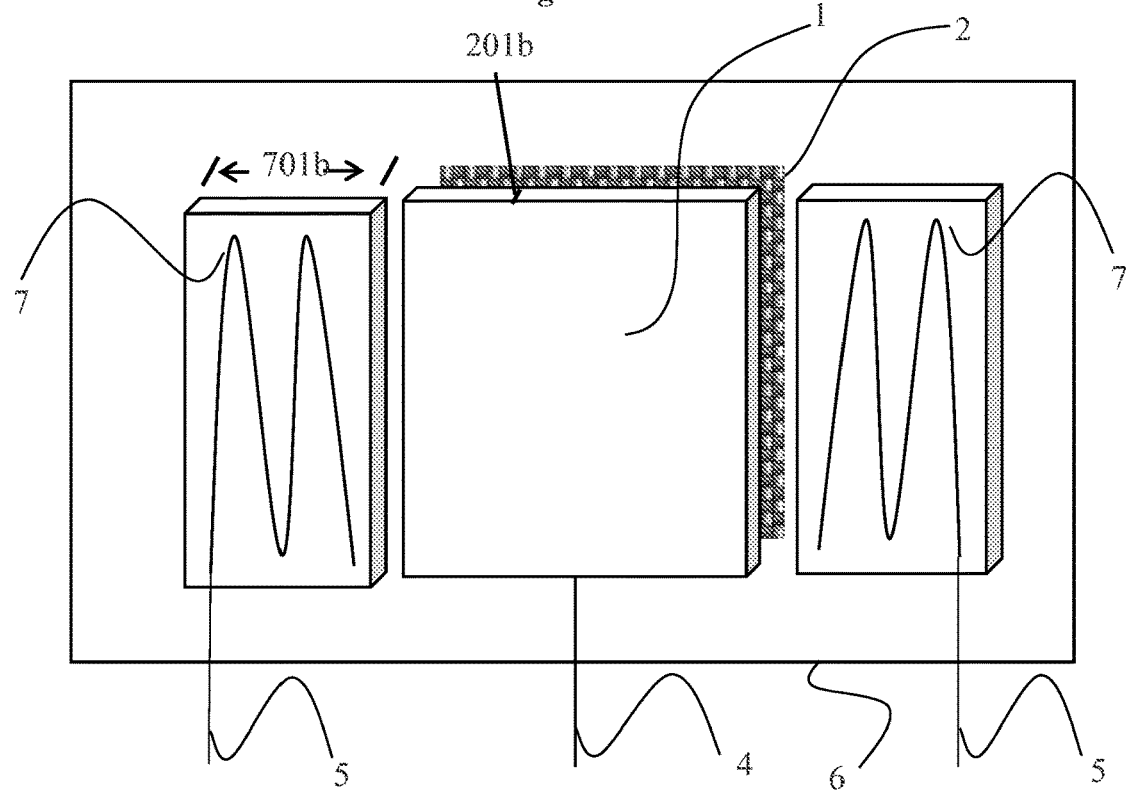
FIG. 2B is a perspective view of an encapsulated EAP shape-morphing sheet system, with one EAP sheet subjected to a positive voltage and two EAP areas wired for complimentary opposable motion, according to one or more embodiments described herein.
Figure 2C:
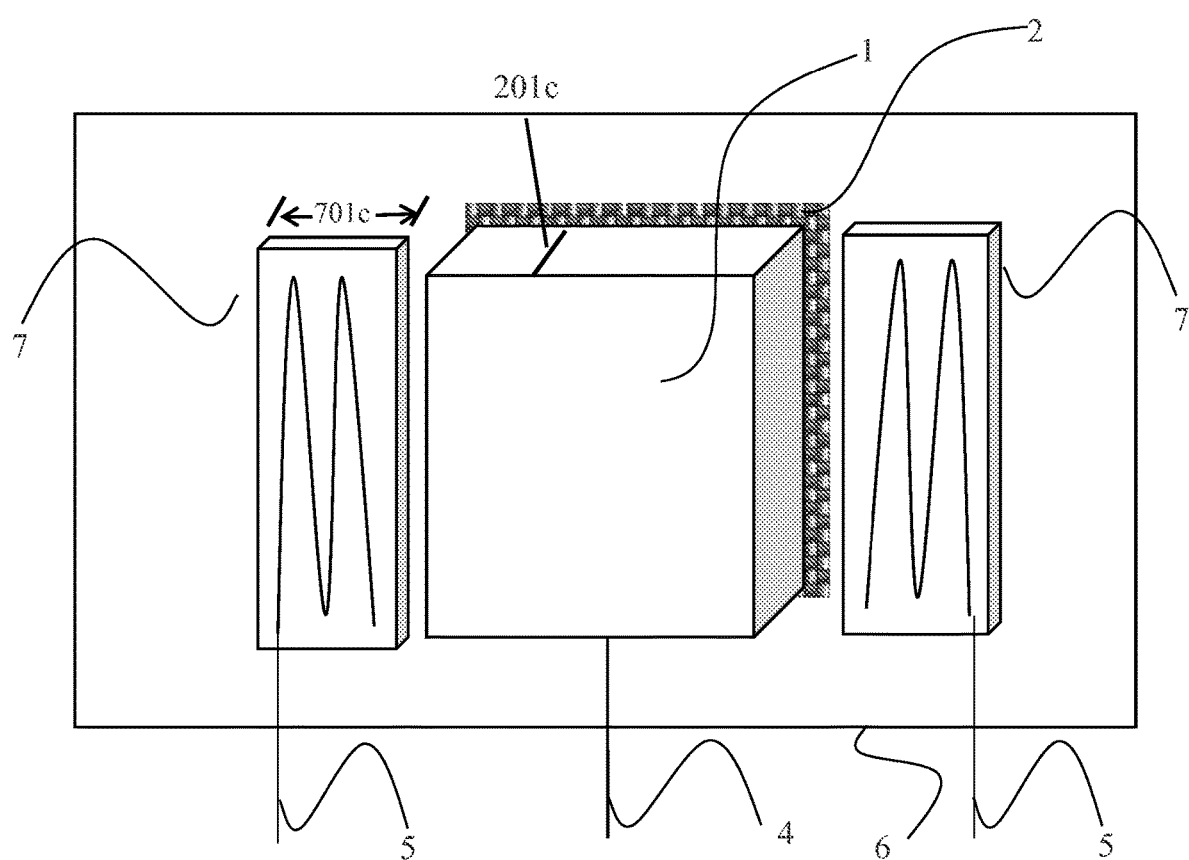
FIG. 2C is a perspective view of an encapsulated EAP shape-morphing sheet system, with one EAP sheet subjected to a negative voltage and two EAP areas wired for complimentary opposable motion, according to one or more embodiments described herein.

During operation, as shown in FIG. 2B, the central EAP sheet is subjected to a positive voltage and thus it contracts perpendicular to the plane of the figure (thickness 201*b* is less than its resting thickness 201*a*). EAP sheet 7, subjected to a negative voltage, will expand parallel to the plant of the figure (i.e., horizontally) (width 701*b* is larger than its resting width 701*a*). Conversely, as shown in FIG. 2C, the central EAP sheet is subjected to a negative voltage and thus it expands (thickness 201*c* is larger than its resting thickness 201*a*). EAP sheet 7, subjected to a positive voltage, will contract parallel to the plant of the figure (i.e., horizontally) (width 701*c* is less than its resting width 701*a*). In certain embodiments, EAP sheets 101 or 201 are bonded to the conductive backing and thus its width may be constricted during expansion or contraction. In certain embodiments, EAP sheet 701 is not bonded to the conductive backing and thus its width is not constricted during expansion or contraction. Thus, as shown in FIGS. 2B and 2C, the width of EAP sheet 701 increases during expansion and decreases during contraction, respectively.

Figure 3:
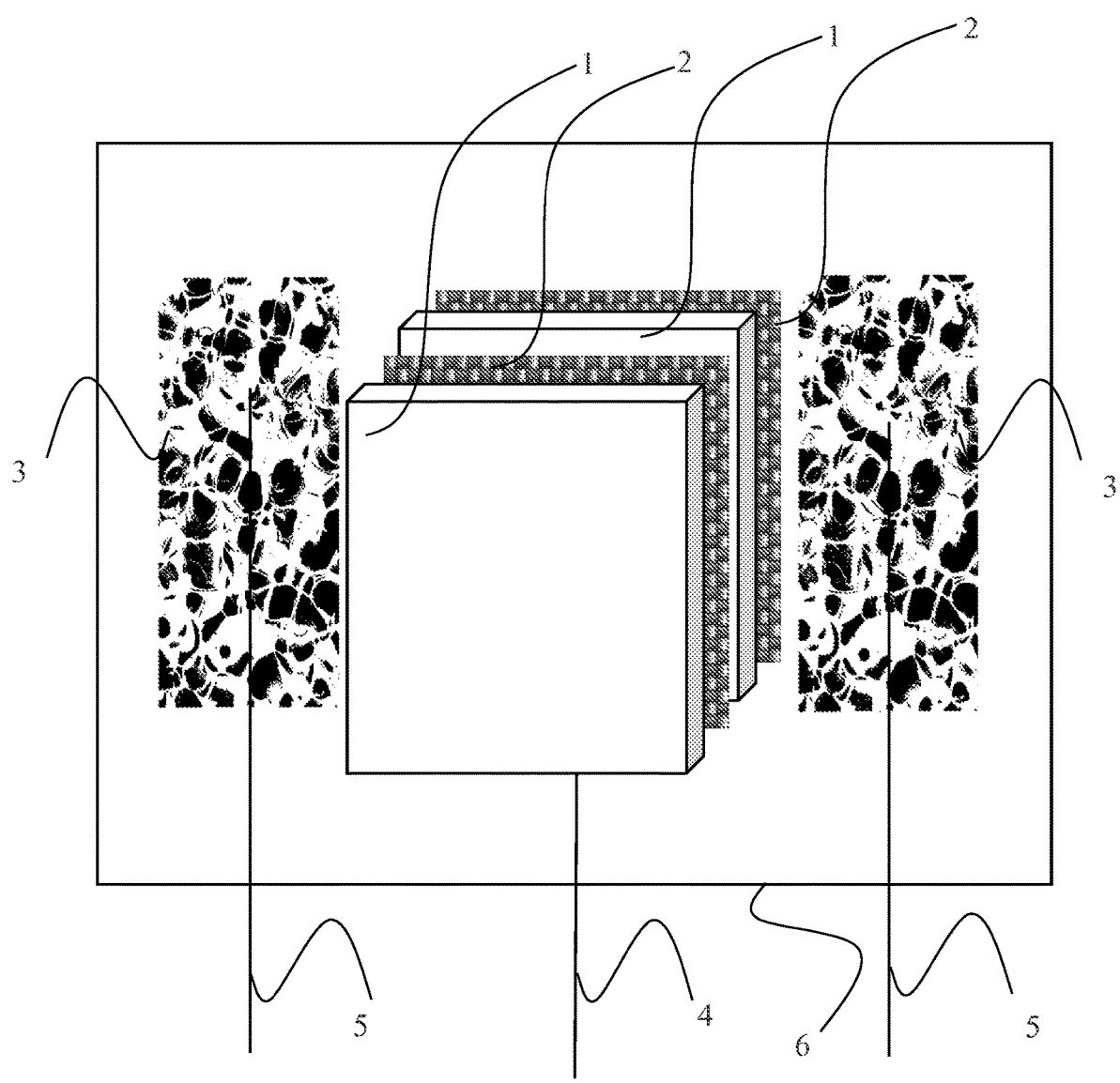
FIG. 3 is a perspective view of an encapsulated electroactive polymer (EAP) shape-morphing pad system, with multiple EAP layers alternated with multiple conductive layers in the system, and with two fluidic reservoirs comprising preferably of open cell foam, according to one or more embodiments described herein.

FIG. 3 shows an encapsulated EAP shape-morphing sheet system having a plurality of the EAP based shape-morphing sheet 1. 2 is the conductive backing to EAP sheet, which can be layered in multiple layers to enhance the overall charge dispersal and enhance the responsiveness of the EAP to the applied voltage, and which with any level of bonding to the EAP sheet(s), provides for a preferential change in thickness of the EAP sheet(s). Additionally, in certain embodiments, increasing the number of the EAP sheet may also increase the overall thickness change. 3 is reservoir areas for fluid, typically water, that absorb or provide moisture from or to the EAP sheet(s) 1 as it shape-morphs, and these reservoir areas are preferably open cell foams. 4 is the electrode connecting to the conductive backing to the EAP sheets and to an electric power source (not shown). 5 is the opposite charged electrodes, conducting the opposite electric polarity charge of electrode 4, connected to the fluidic reservoir areas 3 and to an electric power source (not shown), and 6 is a flexible layer (e.g., a flexible coating layer) of the EAP shape-morphing system comprising preferable medical grade silicone, surrounding above and below and all sides of the EAP shape-morphing system, with flexible or bendable electrodes extending out of the EAP shape-morphing system, but where the flexible or bendable electrodes may be continued within the flexible prosthetic liner.

Figure 4:
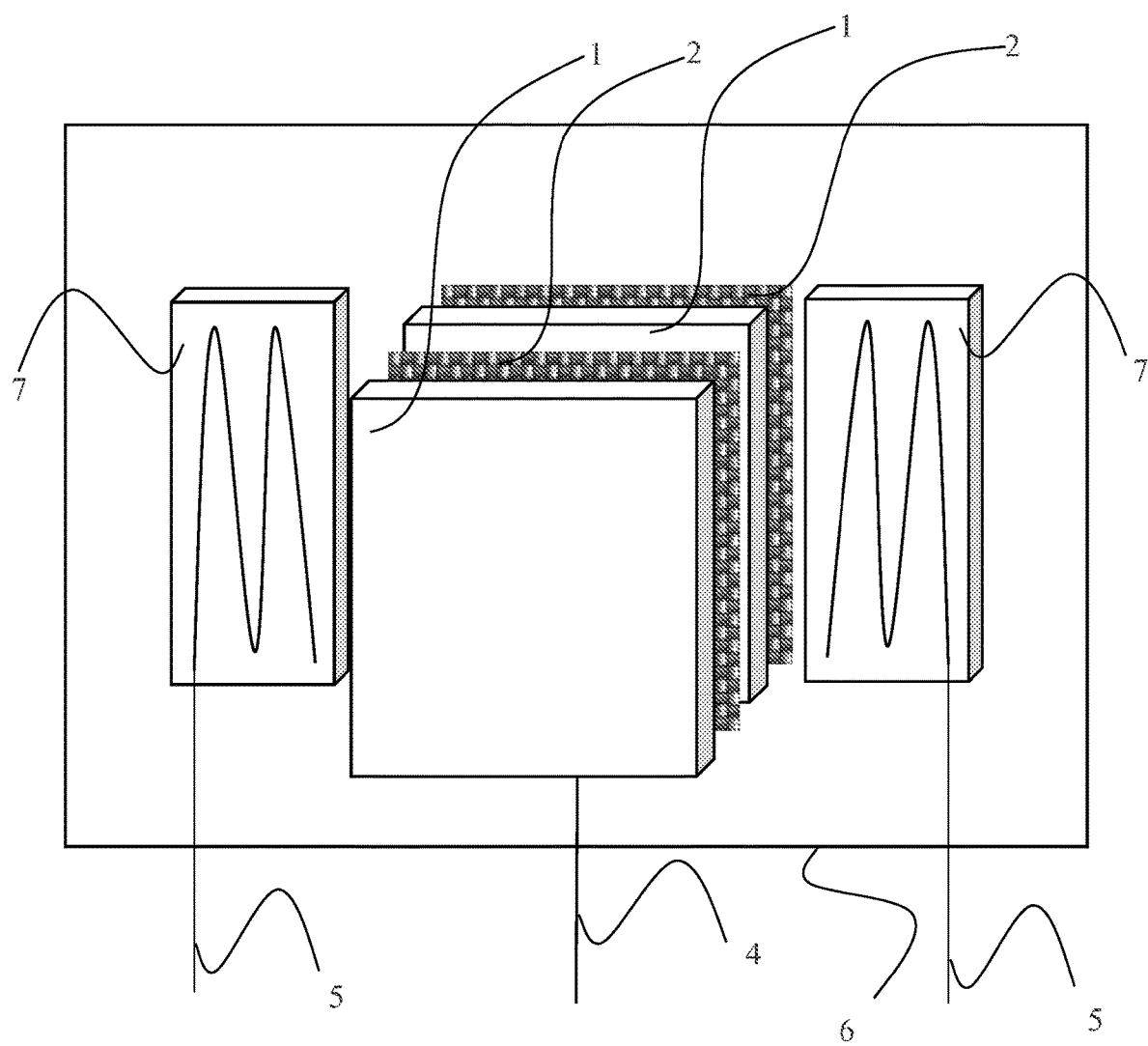
FIG. 4 is a perspective view of another encapsulated EAP shape-morphing pad system, with multiple EAP layers alternated with conductive layers in the system, and two EAP areas wired for complimentary opposable motion, according to one or more embodiments described herein.

FIG. 4 shows an encapsulated EAP shape-morphing sheet system having a plurality of the EAP sheet 1. 2 is the conductive backing to EAP sheet, which can be layered in multiple layers to enhance the overall charge dispersal, and which with any level of bonding to the EAP sheet(s), provides for a preferential change in thickness of the EAP sheets. 7 are opposite motion EAP areas, that absorb or provide moisture from or to the EAP sheet 1 as they shape-morph, and these areas are preferably EAPs with flexible or bendable wiring that allows for change in width in these EAP areas, 4 is the electrode connecting to the conductive backing to the EAP sheets and to an electric power source (not shown), 5 is the opposite charged electrodes, conducting the opposite electric polarity charge of electrode 4, connected to the opposite motion EAP areas 7 and to an electric power source (not shown), and 6 is a flexible layer (e.g., a flexible coating layer) of the EAP shape-morphing sheet system comprising preferable medical grade silicone, surrounding above and below and all sides of the EAP shape-morphing system, with flexible or bendable electrodes extending out of the EAP shape-morphing system, but where the flexible or bendable electrodes may be continued within the flexible prosthetic liner.

Figure 5:
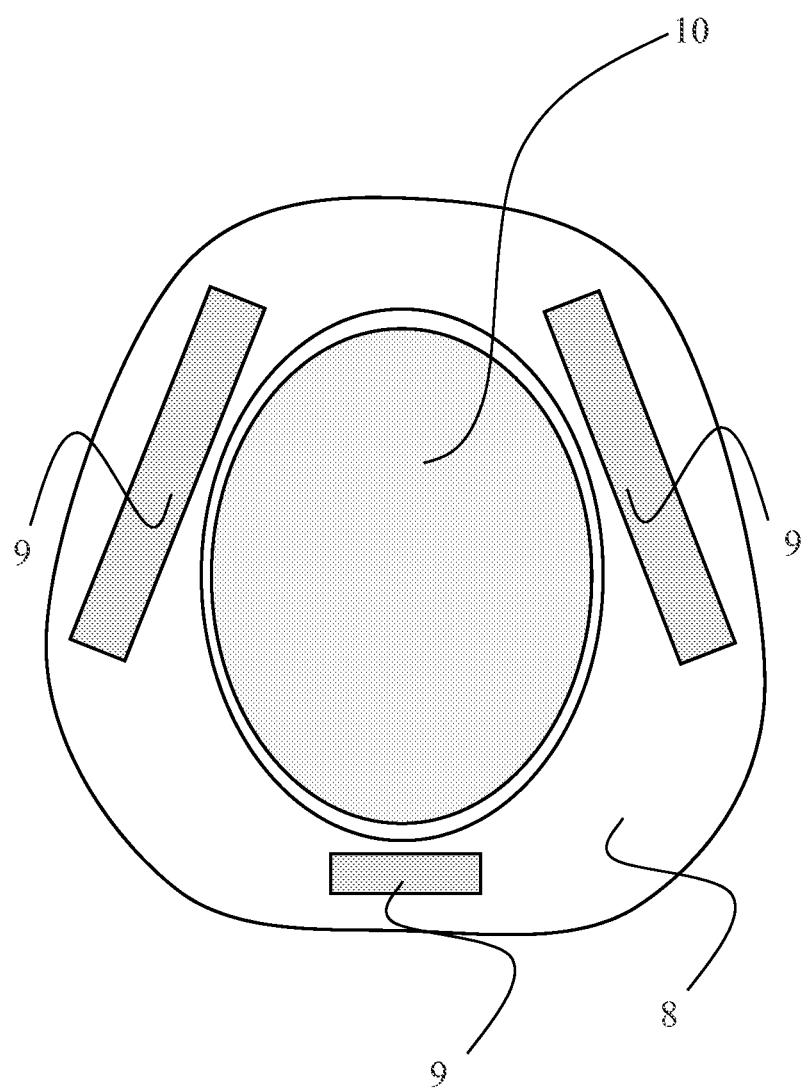
FIG. 5 is a cross-sectional view of the EAP shape-morphing system within a flexible prosthetic liner, according to one or more embodiments described herein.

FIG. 5 shows a top view cross-section of a prosthetic liner 8, with a flexible layer 8 having three encapsulated EAP shape-morphing sheet systems 9 within the flexible layer 8 in strategic positions to maintain comfort and fit by shape-morphing as needed, around the residual limb 10. Flexible or bendable wiring (shown in FIG. 6) connects from the encapsulated EAP shape-morphing pad system(s) 9 to an electric power source (not shown). The strategic positions of the encapsulated EAP shape-morphing sheet system(s) 9 will vary from patient to patient and from the entity of the residual limb, such as upper or lower extremity and above or below the knee amputee, for example. In some embodiments, the prosthetic liner has 1, 2, 3, 4, 5, 6, 7, 8, 9, or 10 encapsulated actuating systems, e.g., EAP shape-morphing sheet systems, within the flexible layer. In some embodiments, the prosthetic liner has 2, 3, or 4 encapsulated actuating systems, e.g., EAP shape-morphing sheet systems, within the flexible layer. Other numbers of the encapsulated actuating systems are contemplated.

In certain embodiments, the prosthetic liner described herein can be worn by a patient between the residual limb and a traditional hard prosthetic device, e.g., a hard body such as a prosthetic hand, arm, foot or leg, carrying the hard body of the prosthesis. In certain embedment, the prosthetic liner's encapsulated EAP shape-morphing actuating systems are designed and arranged to surround the residual limb to provide a secure and comfortable fit.

Figure 6:
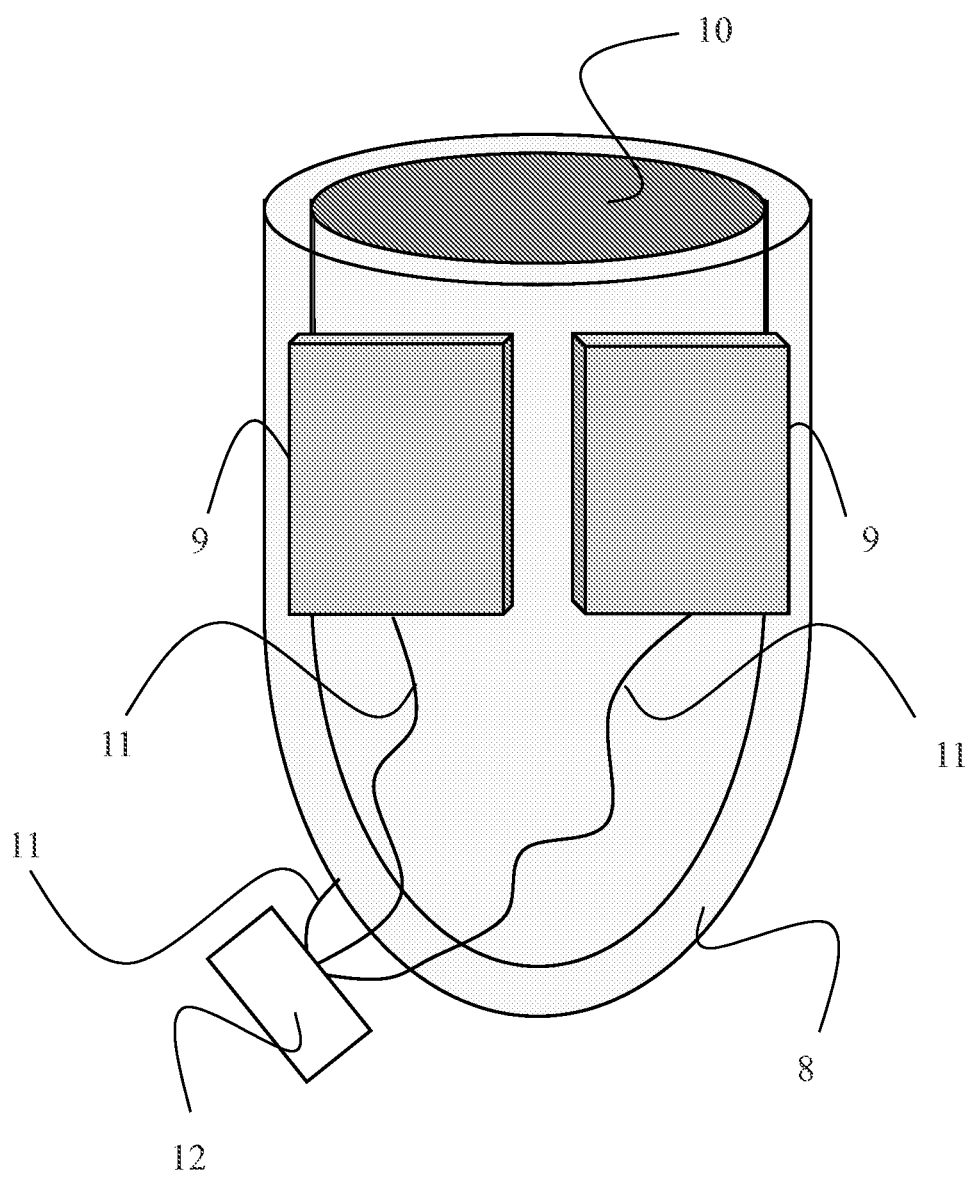
FIG. 6 is a perspective view of the EAP shape-morphing system within a flexible prosthetic liner, according to one or more embodiments described herein.

FIG. 6 shows a perspective view of a prosthetic liner 8, with encapsulated EAP shape-morphing sheet system(s) 9 within the flexible liner 8 in strategic positions to maintain comfort and fit by the encapsulated EAP shape-morphing pad systems 9 shape-morphing as needed, around the residual limb 10. Flexible or bendable wiring 11 connects from the encapsulated EAP shape-morphing sheet system(s) 9 to an electric power source 12, which is preferably a non-rechargeable or rechargeable battery pack or can be directly connected to a wall power outlet. In certain embodiments, the battery pack can be incorporated into the prosthetic liner if space permits or can be external to the prosthetic liner. This placement may vary depending on the size of the liner, pediatric or adult, for example. The strategic positions of the encapsulated EAP shape-morphing pad system(s) 9 will vary from patient to patient and from the entity of the residual limb, such as upper or lower extremity and above or below the knee amputee, for example.

Figure 7:
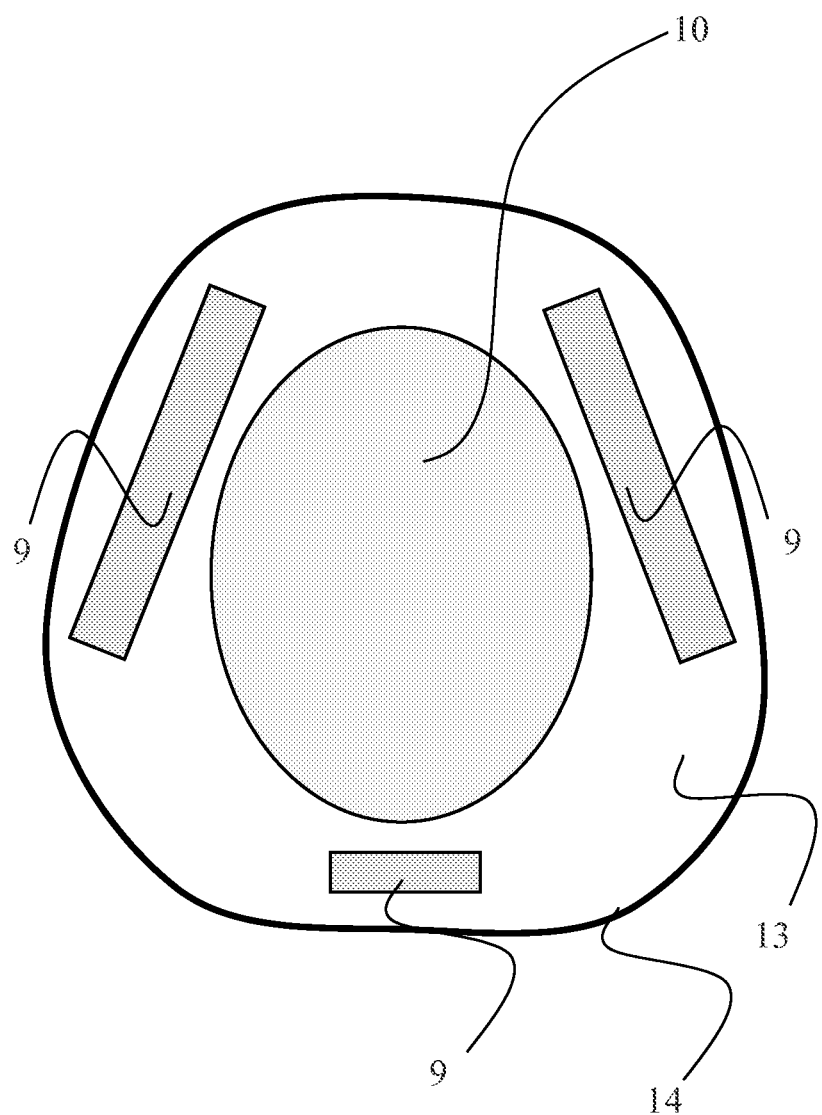
FIG. 7 is a cross-sectional view of the EAP shape-morphing system within a prosthetic socket, according to one or more embodiments described herein.

FIG. 7 shows a top view cross-section of a prosthetic socket 13, with a flexible socket layer 13 having three encapsulated EAP shape-morphing sheet systems 9 within the flexible layer 13 in strategic positions to maintain comfort and fit by shape-morphing as needed, all encased within the hard shell 14 of the prosthetic socket 13, around the residual limb 10. Flexible or bendable wiring (analogous to FIG. 6) connects from the encapsulated EAP shape-morphing pad system(s) 9 to an electric power source (not shown). The strategic positions of the encapsulated EAP shape-morphing sheet system(s) 9 will vary from patient to patient and from the entity of the residual limb, such as upper or lower extremity and above or below the knee amputee, for example. In some embodiments, the prosthetic socket has 1, 2, 3, 4, 5, 6, 7, 8, 9, 10, or more (continuous) encapsulated actuating systems, e.g., EAP shape-morphing sheet systems, within the flexible layer. In some embodiments, the prosthetic socket 2, 3, or 4 encapsulated actuating systems, e.g., EAP shape-morphing sheet systems, within the flexible layer. Other numbers of the encapsulated actuating systems are contemplated.

Figure 8:
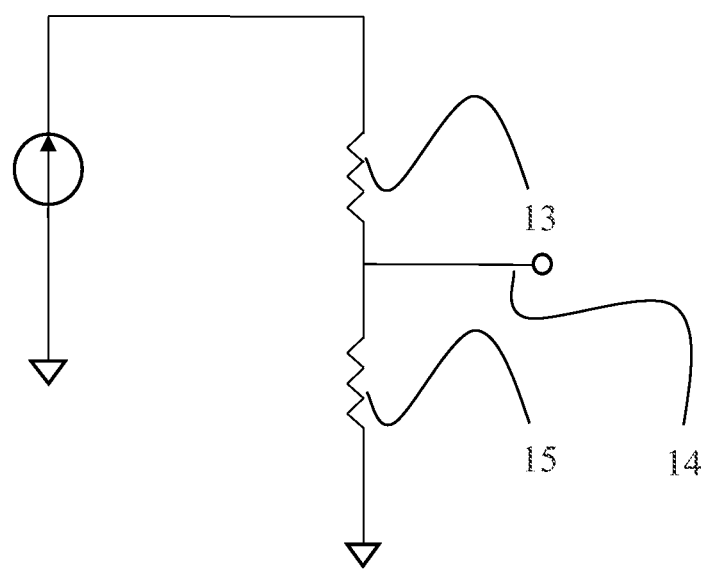
FIG. 8 is a view of the controlled loop circuitry of the EAP pad system for dual use as a sensor, according to one or more embodiments described herein.

FIG. 8 shows the controlled loop circuitry of the EAP pad system for dual use as a sensor, where 13 is the EAP as a resistive sensor (variable sensor) in the circuit, 14 is the $V_{out}$, which is the output voltage, and 15 is the R1, which is the resistor of known resistance. With a known voltage is applied to the circuitry, with known resistance of R1, the resistance or impedance of the EAP can be easily determined under different conditions, such as at different mechanical pressures.

When electricity is applied to the encapsulated EAP shape-morphing sheet system, with positive charged voltage into the EAP based shape-morphing sheet(s) 1, and negative charged voltage into the fluidic reservoirs 2 or opposite motion EAP areas 7, the encapsulated EAP shape-morphing sheet system contracts, and in some embodiments, also widens, allowing for ease in donning the prosthetic liner, typically in the morning. Once the liner is in place, the electric input can be stopped or electric polarity reversed.

In some embodiments, as the residual limb shrinks over the course of the day (typical maintains case), the EAP pads and areas can relax to their original conformations, shape-morphing as the residual limb shrinks (typical case), so that the prosthetic device maintains comfort and good fit throughout the day. In case more expansion of the EAP material is needed, electricity can be manually (e.g., by using the control unit) or automatically applied to the encapsulated EAP shape-morphing sheet system, with reverse polarity, where negatively charged voltage is applied to the EAP based shape-morphing sheet(s) 1, and positive charged voltage is applied into the fluidic reservoirs 2 or opposite motion EAP areas 7, so that the encapsulated EAP shape-morphing system expands more, and in the latter case, also constricts, allowing for even more shape-morphing to maintain comfort and good fit throughout the day. In some embodiments, in the case of the residual limb swelling rather than shrinking during the day (atypical case), the electricity can be manually (e.g., by using the control unit) or automatically applied to the encapsulated EAP shape-morphing system, similar to when donning the liner, with positively charged voltage into the EAP based shape-morphing sheet(s) 1, and negatively charged voltage into the fluidic reservoirs 2 or opposite motion EAP areas 7, so that the encapsulated EAP shape-morphing system contracts, and in the latter case, also widens, to maintain comfort and fit throughout the day.

The encapsulated actuating systems, e.g., EAP shape-morphing sheet systems, shown in FIGS. 1-7 may be used for other shape-morphing and void-filling applications, with or without the encapsulating coating. The EAPs and the encapsulated actuating systems, e.g., EAP shape-morphing sheet systems, can be in a variety of shapes, including but not limited to be spherical, cylindrical, conical, pyramidal, prism-shaped, spheroid, ellipsoid cubical, rectangular prism shaped, toroid, parallelepiped-shaped, rhombic prism shaped, or any combination thereof. The electrodes, which are preferably flexible electrodes, can be incorporated into, touching, or adjacent to the EAPs. In certain embodiments, the electrodes and/or the conductive backing is plasma treated, etched, or otherwise treated, and can be metal based, carbon based, based on other conductive materials, or combinations thereof. In certain embodiments, the electrodes can be in a variety of shapes, such as spiral or spring shaped electrodes, and may be flexible, bendable, or stretchable. The EAP itself or the encapsulated EAP shape-morphing pad systems may be used individually or grouped together in fibers, bulk, slabs, bundles, other configurations, or combinations thereof.

In a further aspect, for the prosthetic liner, the liner itself, rather than using EAP pads, could be constructed entirely or almost entirely with the EAP shape-morphing material, with a grid for electric input, which could be pixelated, so that the entire socket could be shape-morphing.

LIST OF REFERENCE NUMERALS

1—electroactive polymer (EAP) based shape-morphing pad
2—conductive backing (conductive layer) to EAP pad
3—fluidic reservoir
4—electrode
5—opposite charged electrode(s)
6—flexible encapsulating coating
7—opposite motion EAP area
8—surrounding flexible prosthetic liner
9—encapsulated EAP shape-morphing pad system(s)
10—human residual limb
11—flexible or bendable electrode(s)
12—battery pack
13—EAP resistive sensor
14—output voltage $V_{out}$,
15—resistor R1

Electroactive Polymers

In some embodiments, the first electroactive ionic polymer is cross-linked with a first cross-linking polymeric chain. In certain specific embodiments, the first electroactive ionic polymer is an elastomeric polymer chain. Non-limiting examples of the elastomeric polymer chains include a poly (dimethylsiloxane) (PDMS) chain, and a poly(dimethylsiloxane) (PDMS) dimethacrylate chain. In certain specific embodiments, the first electroactive ionic polymer is cross-linked with a first cross-linking polymeric agent comprising a poly(dimethylsiloxane) (PDMS) dimethacrylate chain and a second crossing linking polymeric agent different from the first cross-linking polymeric agent. In some embodiments, the first electroactive ionic polymer is cross-linked with a first cross-linking polymeric chain comprising a poly(dimethylsiloxane) (PDMS) dimethacrylate chain and a second crossing linking polymeric agent different from the first cross-linking polymeric agent. As described herein, the first electroactive ionic polymer may be cross-linked with a first cross-linking polymeric chain and a second crossing linking polymeric agent different from the first cross-linking polymeric agent. In certain embodiments, the first cross-linking polymer agent has elastic characteristics. Non-limiting examples of the first cross-linking polymer agent include a poly(dimethylsiloxane) (PDMS) dimethacrylate polymeric chain. In certain embodiments, the second cross-linking polymeric agent is selected from the group consisting of a poly(ethylene glycol) dimethacrylate chain, an ethylene glycol dimethacrylate, 1,1,1-trimethylolpropane, and a combination thereof. In certain embodiments, the first electroactive ionic polymeric material is selected from the group consisting of polymers of methacrylic acid, copolymers of methacrylic acid and methacrylic acetate salt, such as potassium or sodium salt, other ion-containing polymers or copolymers, and combinations thereof.

Therefore, in these embodiments, the electroactive polymer may be multimodal. That is, the first electroactive ionic polymer may comprise two or more cross-linking polymeric agents and thus have more than one desirable property. In certain specific embodiments, the property is one or more characteristics selected from the group consisting of resistance, elasticity, firmness, shape-morphing ability, resiliency and a combination thereof. Further use of third and/or fourth cross-linking polymer agents different from the first and second cross-lining polymer agents is contemplated. That is, the electroactive polymer may further comprise a fourth cross-linking polymer agent different from the first, second, and third cross-lining polymer agents.

In some embodiments, the first and/or second electroactive ionic polymers are described. The first and/or second electroactive ionic polymers can be polymers of one or more ion-containing monomers or generally any polymer containing one or more ionizable groups. In certain embodiments, the first and/or second electroactive ionic polymers comprise ion-containing monomers such as methacrylic acid, which can also contain polymers comprising non-ionic monomers such as 2-hydroxyethyl methacrylate, cross-linked with poly (ethylene glycol) dimethacrylate or other suitable cross-linking agents, such as ethylene glycol dimethacrylate, 1,1,1-trimethylolpropane trimethacrylate, or a combination of cross-linking agents. Other electroactive polymers may also be used as the electroactive material or as a component of the electroactive material, such as poly(vinyl alcohol), ionized poly(acrylamide), poly(acrylic acid), poly(acrylic acid)-co-(poly(acrylamide), poly(2-acrylamide-2-methyl-1-propane sulfonic acid), poly(methacrylic acid), poly(styrene sulfonic acid), quarternized poly(4-vinyl pyridinium chloride), poly(vinylbenzyltrimethyl ammonium chloride), sulfonated poly(styrene-b-ethylene-co-butylene-b-styrene), sulfonated poly(styrene), or materials that respond to electricity by movement, expansion, contraction, curling, bending, buckling, or rippling. The preferred electroactive material comprises the monomer methacrylic acid, polymerized and cross-linked, preferably with the cross-linking agent poly(ethylene glycol) dimethacrylate with a number average molecular weight around 330 grams per mole, cross-linked at a low level, less than 0.78 mole percent poly(ethylene glycol) dimethacrylate with respect to methacrylic acid, preferably cross-linked within a range of 0.31 to 0.44 mole percent poly(ethylene glycol) dimethacrylate with respect to methacrylic acid. In certain embodiments, prior to polymerization, the monomer and cross-linking agent is diluted with a solvent miscible or compatible with the ion-containing monomer(s). Once polymerized and cross-linked, the electroactive material may be further swollen with an electrolyte solution or electrolyte gel formulation. Other suitable materials and compositions for the electroactive material are described in U.S. Pat. Nos. 8,088,453, 7,935,743, and 5,736,590 and U.S. Ser. Nos. 13/843,959 and 14/476,646, the contents of which are expressly incorporated by reference.

In certain embodiments, different formulations, preferably with respect to cross-linking formulations containing electroactive polymers with different levels of cross-linking, can be used in different regions of the polymer in the prosthetic liner or other actuating or void filling system to provide for different levels of softness, hardness, or shape-morphing as needed. In certain embodiments, multiple cross-linking strategies can be used to provide for multimodality and impact resistance over a wide range of impact scenarios, and to be able to withstand repeated impacts from typical use.

In yet another aspect, an actuation device comprising one or more of the shape-morphing systems disclosed herein is described, wherein upon the application of an electrical potential to the first electrode, the first electroactive ionic polymer is configured to expand or contract to generate an actuation force to result in a movement of at least a portion of the actuation device to move from a first position to a second position.

Method

In yet another aspect, a method of operating a prosthesis is described, comprising:
  providing a prosthesis having a hard body;
  providing the liner of any one of the embodiments described herein;
  providing an electrical potential to the first electrode to
    contract the first electroactive ionic polymer to adjust the fit of the prosthesis to a patient's limb; or
    expand the first electroactive ionic polymer material against the hard body towards the limb of the patient and secure the limb.

In certain embodiments, the voltage is less than about 12.0 V, about 9.0 V, about 6 V, about 5.0 V, about 4.8 V, about 4.5 V, about 4.0 V, about 3.5 V, about 3.0 V, about 2.5 V, about 2.0 V, about 1.5 V, about 1.4 V, about 1.3 V, about 1.25 V, about 1.24 V, about 1.23 V, about 1.21 V, about 1.2 V, about 1.1 V, about 1.0 V, about 0.9 V, or the voltage in a range bounded by any two of the values disclosed herein. In specific embodiments, the voltage is about 1.2 V. In a specific embodiment, the voltage is about 1.23 V.

In certain embodiments, the method further include measuring or receiving the pressure of the first electroactive ionic polymer through a control unit. In certain specific embodiments, the method further includes automatically adjusting the voltage to maintain the pressure to a pre-determined or pre-set value.

In some embodiments, the EAP material within the adjustable liner or socket is contracted when donned in the morning, with a low positive voltage electric input to the material (electrically shielded from the patient), and then allowed to shape and void fill to a set level as it relaxes (absence of electric input) throughout the course of the day, where the original size and thickness of the socket (before contraction, the size and thickness that the EAP based material returns to) is individually designed for the patient to maintain a snug, comfortable fit with no or little maintenance required by the patient as he or she goes about his or her active daily life. Alternatively, once the device is donned, a small negative electric input can be applied to the EAP within the prosthetic liner, to more quickly shape morph and void fill as needed to maintain a comfortable good fit throughout the day. Multi-phasic EAPs can be constructed, where different areas have different levels of stiffness or flexibility, and can shape morph over the course of the day to maintain extremely good comfort and a good fit. In some embodiments, as a precaution, a battery pack is included for initial contraction when donning the prosthetic device, is also there for the patient who experiences the opposite situation over the day, swelling (often seen in diabetic amputees) or to provide for extra expansion as needed, during the course of an extremely active day (dehydration).

FURTHER DESCRIPTION OF EMBODIMENT(S)

In certain specific embodiments, a novel, superior prosthetic liner is disclosed having novel robust electroactive polymers that can controllably change shape by contracting and expanding. Electroactive polymers (EAPs) that can contract and expand are useful for shape-morphing and void-filling applications, but for prosthetic use, which is load bearing, these materials are preferably very robust, in order to support an active lifestyle for amputees.

In yet another aspect, EAP material is disclosed made by incorporating cross-linking agents with elastic characteristics, such as poly(dimethylsiloxane) (PDMS) dimethacrylate into ion-containing polymeric materials from the group consisting of polymers of methacrylic acid, or copolymers of methacrylic acid and methacrylic acetate salt, such as potassium or sodium salt, or other ion-containing polymers or copolymers, or combinations thereof. The resulting EAPs are much tougher (Table 1). This was achieved by the incorporation of a PDMS endcapped with methacrylate to make a dimethacrylate with a functionality of 4 with ion-containing monomers from the group consisting of methacrylic acid, methacrylic acetate salt, such as potassium or sodium salt, or other ion-containing monomers, or combinations thereof, using standard UV photo-polymerization or free radical polymerization methods.

Biological materials are multimodal. This is one reason biological materials, such as cartilage and muscle tissue, can withstand such a wide variety of impact under continual load and use. In order to match prosthetic liners to the residual limb, not only in softness and by shape morphing, but under pressures and loads that would be encountered in prosthetic applications, the EAPs in the instant inventions were also designed to be multi-modal using the following cross-lining strategies: In addition to incorporating PDMS using a PDMS endcapped with methacrylate to make a dimethacrylate with a functionality of 4, multi-modal EAPs were developed using more than one cross-linking agent, for example, using both PDMS endcapped with methacrylate to make a dimethacrylate with a functionality of 4 and poly(ethylene glycol) dimethacrylate (PEG DM). These EAPs using two or more cross-linking agents were tough (FIG. 1) and very impact resistant, withstanding up 4,000 N impact reaction force and withstanding 1,200 cycles of 908 N force repeated impacts, with no discernable adverse effects with respect to material integrity and electroactivity. Noteworthy in Table 1 is that even though the Gen 5 (PDMS dimethacrylate incorporated) EAP and G4/5 (two cross-linking agents incorporated) EAP were stronger and firmer EAPs, these EAPs also had higher percent elongation to break and were much more resilient.

The photo-initiator for all the formulations in Tables 1-4 was 1-hydroxycyclohexyl phenyl ketone (source Sigma-Aldrich, Co., 99% pure, CAS No. 947-19-3), using at least 1 weight percent with respect to the linear monomer methacrylic acid or combination of linear monomers methacrylic acid and methacrylic acetate, sodium or potassium salt. Gen3_1.3 XL PEGDM400 comprised 1.3 weight percent poly(ethylene glycol) dimethacrylate (source Monomer Polymer Dajac Labs, <Mn>~400 g/mole) with respect to linear monomer methacrylic acid. Gen3_3 XL PEGDM400 comprised 3 weight percent poly(ethylene glycol) dimethacrylate (<Mn>~400 g/mole) with respect to linear monomer methacrylic acid. Gen4_2 XL PEGDM400 comprised 1.8 weight percent poly(ethylene glycol) dimethacrylate (<Mn>~400 g/mole) with respect to linear monomer combination of methacrylic acid and methacrylic acetate, potassium salt, where the ratio of the methacrylic acid to methacrylic acetate, K+ salt was 95:5 weight/weight. Gen5_10 XL PDMSDM800 comprised 10 volume percent methacryloxybutyl terminated poly(dimethyl siloxane) (<Mn>~800+/−150 g/mole) with respect to methacrylic acid. G4/5_2 XL PEGDM400_10 XL PDMSDM800 comprised 1.35 weight percent poly(ethylene glycol) dimethacrylate (<Mn>~400 g/mole) and 2.5 volume percent methacryloxybutyl terminated poly(dimethyl siloxane) (<Mn>~800+/−150 g/mole) with respect to linear monomer combination of methacrylic acid and methacrylic acetate, potassium salt, where the ratio of the methacrylic acid to methacrylic acetate, K+ salt was 96.25:3.75 weight/weight. EAP HHC3NST48+ comprised 0.6 weight percent poly (ethylene glycol) dimethacrylate (<Mn>~400 g/mole) and 1.35 weight percent methacryloxybutyl terminated poly (dimethyl siloxane) (<Mn>~800+/−150 g/mole) with respect to methacrylic acid. All EAP formulations were dissolved in water (as the solvent) prior to polymerization at a ratio monomer mixture to water of 1:1 vol/vol, except for G4/5_2 XL PEGDM400_10 XL PDMSDM800 samples, which in the 1:1 vol/vol monomer mix to solvent dilution, had a small amount of acetone mixed in with water in the ratio of acetone to water 1:11 vol/vol. After UV polymerization using either using a custom built UV photo-curing oven with medium wavelength UV radiation, broadly centered between 300 to 450 nm, or Sprectroline® Model SB-100P high intensity UV lamp, centered around 365 nm, all samples were equilibrated in aqueous 0.1 M solution potassium chloride solution. Aqueous 0.1 M KCl solution is the preferred electrolyte solution; however, the electrolyte solution can be from the group comprising any Group 1 or Group 2 and Group 6 and Group 7 salts, ionic liquids, and combinations thereof, neat or in solvent(s).

These EAPs also matched the durometry of humans, in order for the prosthetic liner or socket to have a safe and comfortable fit between the residual limb and the prosthetic device (Table 1). This human-liner interface is of paramount importance for safety and comfort.

TABLE 1

Comparisons of Selected Gen 3, Gen 4, and Gen 5 (PDMS incorporated) and Gen4/5 (2 cross-linking agents) of EAPs that contract and expand, Foam, and Human Interfaces.

| Material/Sample | Durometry Shore O Hardness | Elasticity/Flexibility % Elongation to Break | Electroactive |
|---|---|---|---|
| Gen3_1.3 XL PEGDM400 | 10 | 120 | Yes |
| Gen3_3 XL PEGDM400 | 14 | 120 | Yes |
| Gen4_2 XL PEGDM400 | 15 | 120 | Yes |
| Gen5_10 XL PDMSDM800 | 20 | 150 | Yes |
| G4/5_2 XL PEGDM400_ 10 XL PDMSDM800 | 22 | 200 | Yes |
| Foam* | 40 | 275 | No |
| Human leg, child** | 11$^R$, 16$^C$ | N/A | N/A |
| Human leg, adult*** | 17$^R$, 31$^C$ | N/A | N/A |

*Stiff foam currently used to adjust/shim prostheses
**Measurement taken at skin level of upper leg above knee, healthy 12 year male
***Measurement taken at skin level of upper leg above knee, healthy 52 year female
$^R$= Relaxed muscles
$^C$= Contracted muscles The incorporation of acetate salts, such as methacrylic acetate potassium salt, post-synthesis into the EAP, and the use of layering conductive materials and EAP layers further enhanced electroconductivity, from an electrical impedance of 3 (×20 k scale) Ohms in the control samples to an electrical impedance of 2 Ohm (×20 k scale) Ohms in the experimental samples, which improved the electroactivity, particularly in the second cycle (Table 2), by 2.5-fold increase in contraction and 2-fold increase in expansion.

At the lower voltage levels of 1.2 V: the contraction and with reversed electric polarity, expansion was negligible, even using EAP and conductive alternating layers; and contraction and with reversed electric polarity, expansion was negligible, even with the inclusion of the acetate salts post-synthesis. By using both layers of EAP/conductive alternating layers and by adding acetate salts post-synthetic, the EAP pads are operational and have observable size changes at the very low voltages (less than 1.23 V) required for prosthetic liner applications (Table 3). It is surprisingly find that operation at a voltage less than 1.5 V, e.g., less than 1.23 V, avoids any electrophoresis in these moist EAPs. The methacrylic acetate salt does not mix easily with the PDMS dimethacrylate cross-linking agent, so synthesis was performed at low concentrations of methacrylic acetate salt. By adding more acetate salt post-synthesis, this allows for the control of additional electroactivity.

TABLE 2

Electroactivity of EAP HHC3NST48+, where Control has no post-synthesis additive and Sample 1 has 0.20 g methacrylic acetate potassium salt. Each cycle is 1 minute at 15 V.

| Sample | Polarity of embedded electrode in EAP | Weight (g) | % change from previous cycle | % contraction or expansion |
|---|---|---|---|---|
| Control | No charge | 0.58 | 100% | 0% |
|  | + | 0.56 | 97% | 3% |
|  | − | 0.58 | 104% | 4% |
|  | + | 0.57 | 98% | 2% |
|  | − | 0.58 | 102% | 2% |
| Sample 1 | No charge | 0.58 | 100% | 0% |
|  | + | 0.56 | 97% | 3% |
|  | − | 0.59 | 105% | 5% |
|  | + | 0.56 | 95% | 5% |
|  | − | 0.58 | 104% | 4% |

Note:
EAP HHC3NST48+ is a firm EAP formulation.

TABLE 3

Prosthetic pad testing at 1.2 V using EAP HHC3NST48+ with EA additive and two alternating layers of EAP and conductive layer.

| Polarity of embedded electrode in EAP and time | Weight (g) | % contraction or expansion | EAP Thickness (cm) | % contraction or expansion |
|---|---|---|---|---|
| No Charge | 13.94 | 0% | 1.9 | 0% |
| +, 2 hr | 13.09 | 6% contraction | 1.7 | 11% contraction |
| No charge | 13.09 | 0% | 1.8* | 0% |
| −, 2 hr | 13.40 | 2% expansion | 1.9 | 6% expansion |

*Slight change in height from repositioning after weighing.

The voltage source for the shape-morphing EAP based prosthetic liner pads, liners, or sockets are preferably rechargeable battery packs. The standard operating voltages in prosthetics today are 4.8V, 6V, 9V, and 12V. Because electrophoresis occurs at voltages above 1.23 V, there are two preferable battery system models. One model is to have a stand-alone 1.2V Ni-MH button cell with 320 mAh (0.384 Wh and 1382.4 J). The second preferred system is two 1.2V Ni-MH button cells in parallel to allow an output of 1.2V and 640 mAh (0.768 Wh and 2764.8 J). Other battery systems with multiple 1.2V Ni-MH or 3.6V Li-ion button cells in series or parallel with load voltages of 2.4V, 3.6V and 7.2V are being tested for comparative data. The batteries are not limited to Ni-MH or Li-ion button cells, as there are many types of batteries, but button cells are preferable due to size and limited space in prosthetic liners and sockets.

Pressure sensing occurs from impedance changes in the EAP itself under mechanical pressure. As the EAP is compressed, the impedance decreases (Table 4). The EAPs treated post-synthesis with methacrylic acid potassium salt had even lower impedance values (Table 4). These EAPs can easily serve dual use as resistive pressure sensors, which could be used to provide controlled loop feedback for automatic comfort and good fit throughout the day. This way the patient doesn't even have to think about their prosthetic device as it automatically adjusts during their active life; however, the prosthetic liner or socket should still have manual control so patient can override if needed.

TABLE 4

Comparisons of impedance and change in impedance from mechanical pressure using EAP HHC3NST48+, where Control has no post-synthesis additive and Sample 1 has 0.20 g methacrylic acetate potassium salt.

| Sample | Mechanical Pressure (psi) | Impedance (Ohm) × 20k |
|---|---|---|
| Control | 0 | 3 |
|  | 2.3 | 0.8 |
|  | 4.5 | 0.6 |
|  | 6.8 | 0.5 |
| Sample 1 | 0 | 2 |
|  | 2.3 | 0.6 |
|  | 4.5 | 0.5 |
|  | 6.8 | 0.4 |

The void-filling, shape-morphing abilities and impact resistance lends these novel robust EAPs that can contract and expand for use in prosthetic liners and sockets, and for other void-filling applications. This technology can be used to enhance flexible liners to be more shape adaptive, or could be tailored or even 3D printed to produce extremely comfortable and adaptive custom fit prosthetic liners and sockets.

While for purposes of illustration a preferred embodiments of this invention has been shown and described, other forms thereof will become apparent to those skilled in the art upon reference to this disclosure and, therefore, it should be understood that any such departure from the specific embodiments shown and described are intended to fall within the spirit and scope of this invention.

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

We claim:

1. An electroactive polymer shape-morphing system comprising:
   a first electrode;
   a second electrode counter to the first electrode and spaced apart from the first electrode;
   an ionically conductive fluid; and
   a first actuator electrically connected to the first electrode and comprising a first electroactive ionic polymer, said electroactive polymer selected to expand or contract on application of an electrical potential, and said first actuator spaced apart from and in fluidic communication with the second electrode;
   wherein the shape-morphing system further comprises a fluid reservoir in fluidic communication with the first electroactive ionic polymer and connected to the second electrode; and
   wherein the fluid reservoir comprises a fluid absorption pad or an open cell foam for containing the fluid.

2. The shape-morphing system of claim 1, further comprising an electrically conducting backing disposed along and in electrical contact with a surface of the first actuator, wherein one or both of the first actuator or the backing is electrically connected to the first electrode.

3. The shape-morphing system of claim 2, wherein the surface of the first actuator is bonded to the conducting backing to restrict the contraction or expansion of the first actuator in a direction parallel to the surface.

4. The shape-morphing system of claim 3, wherein the first actuator is configured to contract or expand in a direction perpendicular to the surface.

5. The shape-morphing system of claim 1, wherein the first electroactive ionic polymer is selected to expand or contract in a predetermined direction.

6. The shape-morphing system of claim 5, wherein the actuator has an area and a transverse thickness and the first electroactive ionic polymer is selected to expand or contract the thickness of the actuator.

7. The shape-morphing system of claim 1, wherein the ionically conductive fluid is an aqueous solution of a salt.

8. The shape-morphing system of claim 1, further comprising a second actuator comprising a second electroactive ionic polymer, said second actuator electrically connected to the second electrode and spaced apart from and in fluidic communication with the first electroactive ionic polymer, wherein the first and second electroactive ionic polymers are the same or different.

9. The shape-morphing system of claim 8, wherein the first electroactive ionic polymer is selected to expand and the second electroactive ionic polymer is selected to contract along predetermined directions on application of an electrical potential to the first and second electrodes.

10. The shape-morphing system of claim 8, wherein the first electroactive ionic polymer is selected to contract and the second electroactive ionic polymer is selected to expand along predetermined directions on application of an electrical potential to the first and second electrodes.

11. The shape-morphing system of claim 1, wherein the first actuator is in a shape selected from the group consisting of sheet, pad, sphere, cylinder, cone, pyramid, prism, spheroid ellipse, ellipsoid, rectangular prism, toroid, parallelepiped, rhombic prism and a combination thereof.

12. The shape-morphing system of claim 1, wherein the first actuator comprises one or more electroactive ionic polymer sheets.

13. The shape-morphing system of claim 12, wherein each electroactive ionic polymer sheet is in electrical contact with a conductive layer electrically connected to the first electrode.

14. The shape-morphing system of claim 12, wherein the conductive layer is made from a material selected from the group consisting of metal, carbon, and a combination thereof.

15. The shape-morphing system of claim 1, wherein the first electroactive ionic polymer is selected from the group consisting of polymethacrylic acid, poly2-hydroxyethyl methacrylate, poly(vinyl alcohol), ionized poly(acrylamide), poly(acrylic acid), poly(acrylic acid)-co-(poly(acrylamide), poly(2-acrylamide-2-methyl-1-propane sulfonic acid), poly (methacrylic acid), poly(styrene sulfonic acid), quarternized poly(4-vinyl pyridinium chloride), poly(vinylbenzyltrimethyl ammonium chloride), sulfonated poly(styrene-b-ethylene-co-butylene-b-styrene), sulfonated poly(styrene), and a combination thereof.

16. The shape-morphing system of claim 1, wherein the second electroactive ionic polymer is selected from the group consisting of polymethacrylic acid, poly2-hydroxyethyl methacrylate, poly(vinyl alcohol), ionized poly(acrylamide), poly(acrylic acid), poly(acrylic acid)-co-(poly (acrylamide), poly(2-acrylamide-2-methyl-1-propane sulfonic acid), poly(methacrylic acid), poly(styrene sulfonic acid), quarternized poly(4-vinyl pyridinium chloride), poly (vinylbenzyltrimethyl ammonium chloride), sulfonated poly (styrene-b-ethylene-co-butylene-b-styrene), sulfonated poly (styrene), and a combination thereof.

17. The shape-morphing system of claim 1, wherein the first electroactive ionic polymer is cross-linked with one or more cross-linking polymer agents each selected from the group consisting of a poly(dimethylsiloxane) (PDMS) dimethacrylate chain, a poly(ethylene glycol) dimethacrylate chain, an ethylene glycol dimethacrylate, 1,1,1-trimethylolpropane trimethacrylate, and a combination thereof.

18. The shape-morphing system of claim 1, wherein the first electroactive ionic polymer is cross-linked with one or more elastomeric cross-linking polymer agents.

19. The shape-morphing system of claim 1, wherein the first electroactive ionic polymer is cross-linked with a first cross-linking polymeric chain comprising a poly(dimethylsiloxane) (PDMS) dimethacrylate chain.

20. The shape-morphing system of claim 1, wherein the first electroactive ionic polymer is cross-linked with a first cross-linking polymeric chain comprising a poly(dimethylsiloxane) (PDMS) dimethacrylate chain and a second crossing linking polymeric agent different from the first cross-linking polymeric agent.

21. The shape-morphing system of claim 20, wherein the second cross-linking polymeric agent is selected from the group consisting of a poly(ethylene glycol) dimethacrylate chain, an ethylene glycol dimethacrylate, 1,1,1-trimethylolpropane trimethacrylate, and a combination thereof.

22. The shape-morphing system of claim 1, wherein the first and/or second electrodes are flexible, bendable or stretchable electrodes.

23. The shape-morphing system of claim 1, wherein the first and/or second electrodes are spiral-shaped or spring-shaped.

24. The shape-morphing system of claim 1, wherein the first and/or second electrodes are made from a material selected from the group consisting of metal, carbon, other conductive materials, and a combination thereof.

25. The shape-morphing system of claim 1, further comprising an electroconductivity-enhancing material in ionic communication with the first electroactive ionic polymer.

26. The shape-morphing system of claim 25, wherein the electroconductivity-enhancing material is selected from the group consisting of solvent, electrolyte solution, electrolyte gel formulation, carbon particles, conductive fibers, preceding weaves, preceding felts, preceding nano-particles, preceding nanotubes, metal ions, salt, and a combination thereof.

27. The shape-morphing system of claim 1, further comprising a power source.

28. The shape-morphing system of claim 27, wherein the power source is a rechargeable or non-rechargeable battery pack.

29. The shape-morphing system of claim 1, wherein the shape-morphing system is in a form selected from the group consisting of fibers, bulk, slabs, bundles, and combinations thereof.

30. The shape-morphing system of claim 1, configured for filling a void between the first actuator and a target element.

31. The shape-morphing system of claim 1, configured for securing or engaging a target element.

32. A liner for securing a limb in a prosthetic device or a prosthetic socket comprising:
a flexible layer configured to surround a limb of a patient or conform to the inside circumference of a prosthesis; and
at least one shape-morphing system of claim 1 embedded in the flexible layer and configured to secure or engage a limb of a patient.

33. The liner or prosthetic socket of claim 32, wherein the flexible layer is made of silicone.

34. The liner or prosthetic socket of claim 32, wherein the liner or prosthetic socket comprises a plurality of the shape-morphing systems each of any one of the preceding claims and embedded in the flexible layer; wherein the shape-morphing systems are fluidically isolated from each other and arranged around the limb of a patient to secure the limb.

35. The liner or prosthetic socket of claim 32, wherein the prosthesis has a hard body and upon the application of an electrical potential to the first electrode, the first actuator is configured to expand against the hard body towards the limb of the patient.

36. The liner or prosthetic socket of claim 32, further comprises a control unit configured to receive or measure the impedance and/or the pressure of the first electroactive ionic polymer.

37. The liner or prosthetic socket of claim 36, wherein the control unit automatically adjusts the voltage of the first electrode to adjust the pressure of the first electroactive ionic polymer.

38. The liner or prosthetic socket of claim 37, wherein the control unit is configured to adjust the pressure to a pre-determined value or a pre-set value.

39. An actuation device comprising one or more of the shape-morphing systems of claim 1, wherein upon the application of an electrical potential to the first electrode, the first electroactive ionic polymer is configured to expand or contract to generate an actuation force to result in a movement of the first actuator to move from a first position to a second position.

40. A method of operating a prosthesis, comprising:
providing a prosthesis having a hard body;
providing the liner of claim 27,
providing an electrical potential to the first electrode to contract the first electroactive ionic polymer to adjust the fit of the prosthesis to a patient's limb; or
expand the first electroactive ionic polymer material against the hard body towards the limb of the patient and secure the limb.

41. The method of claim 40, wherein the first electroactive ionic polymer is subjected to a voltage of less than about 1.23 V.

42. The method of claim 41, further comprising measuring or receiving the pressure of the first electroactive ionic polymer through a control unit.

43. The method of claim 42, further comprising automatically adjusting the voltage to maintain the pressure to a pre-determined or pre-set value.

44. The method of claim 40, wherein the first electroactive ionic polymer is subjected to a voltage of from about 1.23 V to about 12 V.

45. The method of claim 40, wherein the first electroactive ionic polymer is subjected to a voltage of from about 1.5 V to about 6 V.

46. The method of claim 40, wherein the first electroactive ionic polymer is subjected to a voltage of from about 1.5 V to about 3 V.

47. The method of claim 40, wherein the first electroactive ionic polymer is subjected to a voltage of from about 3 V to about 5 V.

48. The method of claim 40, wherein the first electroactive ionic polymer is subjected to a voltage of from about 5 V to about 6 V.

49. The method of claim 44, further comprising measuring or receiving the pressure of the first electroactive ionic polymer through a control unit.

50. The method of claim 49, further comprising automatically adjusting the voltage to maintain the pressure to a pre-determined or pre-set value.

* * * * *